(12) United States Patent
Prinz et al.

(10) Patent No.: US 12,097,277 B2
(45) Date of Patent: Sep. 24, 2024

(54) HYDROGEL COMPOSITION COMPRISING A CROSSLINKED POLYMER

(71) Applicant: CROMA-PHARMA GMBH, Leobendorf (AT)

(72) Inventors: Martin Prinz, Klosterneuburg (AT); Ralph Hollaus, Vienna (AT); Robert Sachsenhofer, Vienna (AT)

(73) Assignee: CROMA-PHARMA GMBH, Leobendorf (AT)

( * ) Notice: Subject to any disclaimer, the term of this patent is extended or adjusted under 35 U.S.C. 154(b) by 728 days.

(21) Appl. No.: 17/252,532

(22) PCT Filed: Jun. 14, 2019

(86) PCT No.: PCT/EP2019/065755
§ 371 (c)(1),
(2) Date: Dec. 15, 2020

(87) PCT Pub. No.: WO2019/238954
PCT Pub. Date: Dec. 19, 2019

(65) Prior Publication Data
US 2021/0260243 A1 Aug. 26, 2021

(30) Foreign Application Priority Data

Jun. 15, 2018 (EP) .................................... 18178097
Jun. 15, 2018 (EP) .................................... 18178098
Jun. 15, 2018 (EP) .................................... 18178099

(51) Int. Cl.
| | | |
|---|---|---|
| *A61K 31/728* | (2006.01) | |
| *A61K 8/04* | (2006.01) | |
| *A61K 8/73* | (2006.01) | |
| *A61K 45/06* | (2006.01) | |
| *A61K 47/06* | (2006.01) | |
| *A61L 27/20* | (2006.01) | |
| *A61L 27/52* | (2006.01) | |
| *A61L 31/04* | (2006.01) | |
| *A61L 31/14* | (2006.01) | |
| *C08L 5/08* | (2006.01) | |

(52) U.S. Cl.
CPC .............. *A61K 8/735* (2013.01); *A61K 8/042* (2013.01); *A61K 31/728* (2013.01); *A61K 45/06* (2013.01); *A61K 47/06* (2013.01); *A61L 27/20* (2013.01); *A61L 27/52* (2013.01); *A61L 31/042* (2013.01); *A61L 31/145* (2013.01); *C08L 5/08* (2013.01); *A61L 2300/236* (2013.01); *A61L 2300/402* (2013.01); *A61L 2400/06* (2013.01); *A61L 2430/34* (2013.01)

(58) Field of Classification Search
CPC .......... A61K 8/735; A61K 8/042; A61K 8/06; A61K 31/728; A61K 45/06; A61K 47/06; A61K 47/36; A61K 2800/91; A61L 27/20; A61L 27/52; A61L 31/042; A61L 31/145; A61L 2300/236; A61L 2300/402; A61L 2400/06; A61L 2430/34; A61L 27/50; C08L 5/08; A61Q 19/08; A61P 1/00; A61P 3/04; A61P 9/00; A61P 13/00; A61P 15/00; A61P 15/02; A61P 15/12; A61P 17/00; A61P 17/02; A61P 29/00
See application file for complete search history.

(56) References Cited

U.S. PATENT DOCUMENTS

| | | | |
|---|---|---|---|
| 4,582,865 | A | 4/1986 | Balazs et al. |
| 6,884,788 | B2 | 4/2005 | Bulpitt et al. |
| 2002/0071855 | A1 | 6/2002 | Sadozai et al. |
| 2004/0059066 | A1 | 3/2004 | Yamamoto |
| 2008/0025950 | A1 | 1/2008 | Prestwich et al. |
| 2008/0221062 | A1 | 9/2008 | Miyamoto et al. |
| 2008/0292703 | A1 | 11/2008 | Renier et al. |
| 2009/0093414 | A1 | 4/2009 | Ikeya et al. |
| 2009/0269417 | A1 | 10/2009 | Gonzalez et al. |
| 2012/0034271 | A1 | 2/2012 | Shu |
| 2013/0123210 | A1 | 5/2013 | Liu et al. |
| 2013/0210760 | A1 | 8/2013 | Liu et al. |
| 2016/0038396 | A1 | 2/2016 | Tezel et al. |

(Continued)

FOREIGN PATENT DOCUMENTS

| | | | | |
|---|---|---|---|---|
| CA | 2348842 | A1 | 5/2000 | |
| CA | 2673323 | A1 * | 7/2008 | ............. A61K 8/735 |
| CN | 101367884 | A * | 2/2009 | |

(Continued)

OTHER PUBLICATIONS

Ding et al., Multilayered mucoadhesive hydrogel films based on thiolated hyaluronic acid and polyvinylalcohol for insulin delivery, Jun. 26, 2012, Acta Biomaterialia, vol. 8, pp. 3643-3651. (Year: 2012).*

Shu et al., "Synthesis and evaluation of injectable, in situ crosslinkable synthetic extracellular matrices for tissue engineering", Journal of Biomedical Materials Research Part A, Dec. 15, 2006, pp. 902-912.

Bernkop-Schnürch, A. and T. E. Hopf (2001). "Synthesis and in Vitro Evaluation of Chitosan-Thioglycolic Acid Conjugates." *Scientia Pharmazeutica* 69: 109-118.

Bernkop-Schnürch, A., C. E. Kast and M. F. Richter (2001). "Improvement in the mucoadhesive properties of alginate by the covalent attachment of cysteine." *J Control Release* 71(3): 277-285.

(Continued)

*Primary Examiner* — Ali Soroush
(74) *Attorney, Agent, or Firm* — Workman Nydegger

(57) ABSTRACT

A sterile hydrogel composition comprising a crosslinked polymer, wherein the crosslinked polymer is an oxidation product of a thiol-modified hyaluronan and wherein the thiol-modified hyaluronan has a degree of modification of hyaluronan with thiol moieties of more than about 80 μmol per gram polymer, wherein the thiol-modified hyaluronan has a degree of modification of hyaluronan with thiol moieties of less than about 280 μmol per gram polymer, wherein the composition has a residual thiol content of less than 20% in respect to the degree of modification of the thiol-modified hyaluronan.

20 Claims, 2 Drawing Sheets

(56) References Cited

U.S. PATENT DOCUMENTS

Figure 1:
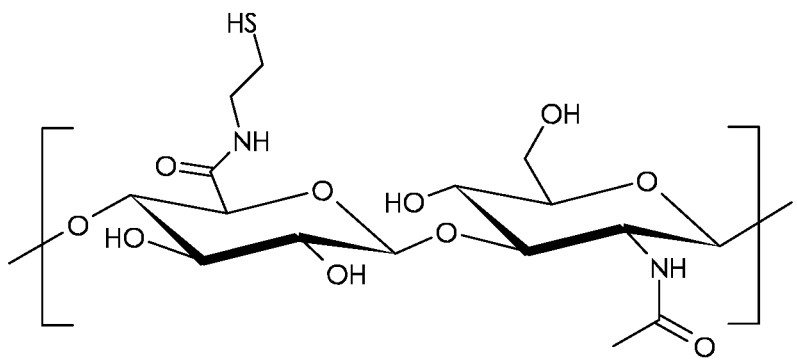

| | | | |
|---|---|---|---|
| 2016/0220729 | A1 | 8/2016 | Gousse et al. |
| 2019/0270829 | A1 | 9/2019 | Zeng et al. |

FOREIGN PATENT DOCUMENTS

| | | | | |
|---|---|---|---|---|
| CN | 101622017 | A | 1/2010 | |
| CN | 101721349 | | 6/2010 | |
| CN | 102399295 | A | 4/2012 | |
| CN | 104892962 | | 9/2015 | |
| CN | 107412002 | | 12/2017 | |
| EA | 013877 | | 8/2008 | |
| EP | 0587715 | A1 | 3/1994 | |
| EP | 1115433 | B1 | 12/2004 | |
| EP | 1790665 | A1 | 5/2007 | |
| EP | 2103631 | A1 | 9/2009 | |
| EP | 2614828 | | 7/2013 | |
| JP | 2012521270 | | 9/2012 | |
| WO | 92/20349 | A1 | 11/1992 | |
| WO | WO2003080135 | | 10/2003 | |
| WO | 2002056914 | A1 | 5/2004 | |
| WO | WO2004037164 | | 5/2004 | |
| WO | WO2005056608 | | 6/2005 | |
| WO | 2008/008857 | A2 | 1/2008 | |
| WO | 2005095464 | A1 | 2/2008 | |
| WO | WO 2008077172 | | 7/2008 | |
| WO | 2008148071 | | 12/2008 | |
| WO | WO 2009005790 | | 1/2009 | |
| WO | WO-2009005790 | A2 * | 1/2009 | ............ A61L 27/20 |
| WO | WO2009108100 | | 9/2009 | |
| WO | 2010111161 | | 9/2010 | |
| WO | WO2012167079 | | 12/2012 | |
| WO | WO2013086024 | | 6/2013 | |
| WO | 2014/064632 | A1 | 5/2014 | |
| WO | WO2014181147 | | 11/2014 | |
| WO | WO2016005785 | | 1/2016 | |
| WO | 2018/083326 | A1 | 5/2018 | |
| WO | 2019/238954 | A1 | 12/2019 | |

OTHER PUBLICATIONS

Bernkop-Schnürch, A., V. Schwarz and S. Steininger (1999). "Polymers with thiol groups: a new generation of mucoadhesive polymers?" *Pharm Res* 16(6): 876-881.

Bernkop-Schnürch, A. (2005). "Thiomers: a new generation of mucoadhesive polymers." *Adv Drug Deliv Rev* 57(11): 1569-1582.

Kast, C. E. and A. Bernkop-Schnurch (2001). "Thiolated polymers—thiomers: development and in vitro evaluation of chitosan-thioglycolic acid conjugates." *Biomaterials* 22(17): 2345-2352.

Kast, C. E. and A. Bernkop-Schnurch (2002). "Polymer-cysteamine conjugates: new mucoadhesive excipients for drug delivery?" *Int J Pharm* 234(1-2): 91-99.

Krauland, A. H., M. H. Hoffer and A. Bernkop-Schnurch (2005). "Viscoelastic properties of a new in situ gelling thiolated chitosan conjugate." *Drug Dev Ind Pharm* 31(9): 885-893.

Marschütz, M. K. and A. Bernkop-Schnürch (2002). "Thiolated polymers: self-crosslinking properties of thiolated 450 kDa poly(acrylic acid) and their influence on mucoadhesion." *European Journal of Pharmaceutical Sciences* 15(4): 387-394.

Palmberger, T. F., K. Albrecht, B. Loretz and A. Bernkop-Schnürch (2007). "Thiolated polymers: Evaluation of the influence of the amount of covalently attached 1-cysteine to poly(acrylic acid)." *European Journal of Pharmaceutics and Biopharmaceutics* 66(3): 405-412.

Perera, G., J. Hombach and A. Bernkop-Schnurch (2010). "Hydrophobic thiolation of pectin with 4-aminothiophenol: synthesis and in vitro characterization." *AAPS PharmSciTech* 11(1): 174-180.

Ågerup, B., P. Berg and C. Åkermark (2005). "Non-Animal Stabilized Hyaluronic Acid." *BioDrugs* 19(1): 23-30.

Bae, H. D., L. J. Yanke, K. J. Cheng and L. B. Selinger (1999). "A novel staining method for detecting phytase activity." *J Microbiol Methods* 39(1): 17-22.

Beasley, K. L., M.A. Weiss, R. A. Weiss (2009). "Hyaluronic acid fillers: a comprehensive review. " *Facial Plast Surg* 25:86-94.

Bothner, H., T. Waaler and O. Wik (1988). "Limiting viscosity number and weight average molecular weight of hyaluronate samples produced by heat degradation." *International Journal of Biological Macromolecules* 10(5): 287-291.

Choi, J.-i., J.-K. Kim, J.-H. Kim, D.-K. Kweon and J.-W. Lee (2010). "Degradation of hyaluronic acid powder by electron beam irradiation, gamma ray irradiation, microwave irradiation and thermal treatment: a comparative study." *Carbohydrate Polymers* 79(4): 1080-1085.

Edsman, K., Å. Öhrlund, C. Sturesson, L. Nord, A. H. Kenne and J. Näsström (2010). The Difference Between Stabilization and Crosslinking. *8th Anti-aging Medicine World Congress (AMWC)*. Monaco.

Jones, D. S. (2009). Chitosan. *Handbook of Pharmaceutical Excipients Sixth Edition*. R. C. Rowe, P. J. Sheskey and M. E. Quinn. London Chicago, Pharmaceutical Press: 159-161.

Liu, N., L. Shao, X. Xu, J. Chen, H. Song, Q. He, Z. Lin, L. Zhang and C. B. Underhill (2002). "Hyaluronan metabolism in rat tail skin following blockage of the lymphatic circulation." *Lymphology* 35(1): 15-22.

Liu, Y., X. Zheng Shu and G. D. Prestwich (2005). "Biocompatibility and stability of disulfide-crosslinked hyaluronan films." *Biomaterials* 26(23): 4737-4746.

Lowry, K. M. and E. M. Beavers (1994). "Thermal stability of sodium hyaluronate in aqueous solution." *J Biomed Mater Res* 28(10): 1239-1244.

Mason, C., P. Dunnhill (2008). "A brief definition of regenerative medicine." *Regen Med* 3(1):1-5.

May, B. C., A. T. Fafarman, S. B. Hong, M. Rogers, L. W. Deady, S. B. Prusiner and F. E. Cohen (2003). "Potent inhibition of scrapie prion replication in cultured cells by bis-acridines." *Proc Natl Acad Sci U S A* 100(6): 3416-3421.

Peppas, N. A. (1991). "Physiologically Responsive Hydrogels." *Journal of Bioactive and Compatible Polymers* 6(3): 241-246.

Prestwich, G. D., D. M. Marecak, J. F. Marecek, K. P. Vercruysse and M. R. Ziebell (1998). "Controlled chemical modification of hyaluronic acid: synthesis, applications, and biodegradation of hydrazide derivatives." *Journal of Controlled Release* 53(1): 93-103.

Quinn, M. E. and P. J. Sheskey (2009). Sodium Hyaluronate. *Handbook of Pharmaceutical Excipients Sixth Edition*. R. C. Rowe, P. J. Sheskey and M. E. Quinn. London Chicago, Pharmaceutical Press: 646-648.

Serban, M. A., G. Yang and G. D. Prestwich (2008). "Synthesis, characterization and chondroprotective properties of a hyaluronan thioethyl ether derivative." Biomaterials 29(10): 1388-1399.

Shu, X. Z., Y. Liu, Y. Luo, M. C. Roberts and G. D. Prestwich (2002). "Disulfide cross-linked hyaluronan hydrogels." Biomacromolecules 3(6): 1304-1311.

Shu, X. Z., Y. Liu, F. Palumbo and G. D. Prestwich (2003). "Disulfide-crosslinked hyaluronan-gelatin hydrogel films: a covalent mimic of the extracellular matrix for in vitro cell growth." *Biomaterials* 24(21): 3825-3834.

Sparer, R. V., N. Ekwuribe and A. G. Walton (1983). Controlled Release from Glycosaminoglycan Drug Complexes. *Controlled Release Delivery Systems*. T. J. Roseman and S. Z. Mansdorf. New York and Basel, Marcel Dekker, Inc.

The international pharmacopoeia [ electronic resource]—9th ed. (2019). Methods of sterilization. Geneva, World Health Organization.

La Gatta, A. et al., 2016, "Biophysical and biological characterization of a new line of hyaluronan-based dermal fillers: a scientific rationale to specific clinical indications", Materials Science and Engineering C 68: 565-572.

Shu, X. Z., S. Ahmad, Y. Liu, and G. D. Prestwich (2006). "Synthesis and evaluation of injectable, in situ crosslinkable synthetic extracelluar matrices for tissue engineering." J Biomed Mater Res A 79(4):902-12.

Ding et al., Multilayered mucoadhesive hydrogel films based on thiolated hyaluronic acid and polyvinylalcohol for insulin delivery, Acta Biomaterialia, vol. 8, pp. 3643-3651. (Year: 2012).

(56) References Cited

OTHER PUBLICATIONS

Bernuzzi et al., "An innovative way to thermally sterilize hyaluronic acid pre-filled syringes", 2016 white paper available under https://demo6.esoul.it/wp-content/uploads/2019/07/WP_Thermal_Sterilization_PFS_with_Hyaluronic_Acid.pdf.
Cowman et al., "Improved agarose gel electrophoresis method and molecular mass calculation for high molecular mass hyaluronan, Analytical Biochemistry", vol. 417, No. 1, 2011, pp. 50-56.
Gatta et al., "Biophysical and biological characterization of a new line of hyaluronan-based dermal fillers: a scientific rationale to specific clinical indications", Materials Science and Engineering C, vol. 68, 2016, pp. 565-572.
Hoet et al., "Polyamines in the lung: polyamine uptake and polyamine-linked pathological or toxicological conditions", Am. J. Physiol. Lung Cell. Mol. Physiol., vol. 278, No. 3, 2000, pp. L417-L433.
International Preliminary Report on Patentability received for PCT Patent Application No. PCT/EP2019/065754, mailed on Dec. 24, 2020, 7 pages.
International Search Report and Written Opinion received for PCT Patent Application No. PCT/EP2020/087140, mailed on Apr. 26, 2021, 11 pages.
International Search Report issued in PCT/EP2019/065754, dated Sep. 20, 2019.
International Search Report issued in PCT/EP2019/065756 mailed Oct. 1, 2019.
Kafedjiiski et al., "Synthesis and in vitro evaluation of thiolated hyaluronic acid for mucoadhesive drug delivery", Int. J. Pharm., vol. 343, 2007, pp. 48-58.
Kafedjiiski, et al, "Synthesis and in vitro evaluation of thiolated hyaluronic acid for mucoadhesive drug delivery" International Journal of Pharmaceutics, Eslevier, NL vol. 343, No. 1-2, Aug. 30, 2007.
Stocks D. et al, "Rheological Evaluation of the Physical Properties of Hyaluronic Acid Dermal Fillers," J Drugs Dermatol, vol. 10, Issue 9, 2011, pp. 974-980.
The international gharmacogoeia [electronic resource]—9th ed. (2019). Methods of sterilization. Geneva, World Health Organization.
Aufort et al., "Oxorhenium-Mediated Assembly of Noncyclic Selective Integrin Antagonists: a Combinatorial Approach", ChemBioChem, vol. 12, Issue 4, 2011, pp. 583-592.
Borke et al., "Optimized triazine-mediated amidation for efficient and controlled functionalization of hyaluronic acid", Carbohydrate Polymers, vol. 116, 2015, pp. 42-50.
Boulle et al., "A review of the metabolism of 1,4-butanediol diglycidyl ether-crosslinked hyaluronic acid dermal fillers", Dermatol. Surg., vol. 39, No. 12, 2013, pp. 1758-1766.
Choi et al., "Modulation of biomechanical properties of hyaluronic acid hydrogels by crosslinking agents", J. Biomed. Mater Res. Part A, vol. 103, No. 9, 2015, pp. 3072-3080.
Cowman M.K. et al, "Improved agarose gel electrophoresis method and molecular mass calculation for high molecular mass hyaluronan," Analytical Biochemistry, vol. 417, 2011, pp. 50-56.
Griesser et al., "Thiolated Hyaluronic Acid as Versatile Mucoadhesive Polymer: From the Chemistry Behind to Product Developments—What Are the Capabilities?", Polymers, vol. 10, No. 3, 2018, 16 Pages.
Hoet P. H.M et al, "Polyamines in the lung: polyamine uptake and polyamine-linked pathological or toxicological conditions," Am. J. Physiol. Lung Cell. Mol. Physiol, vol. 278, 2000, pp. L417-L433.
Liang et al., "Investigating triazine-based modification of hyaluronan using statistical designs", Carbohydrate Polymers, vol. 132, Issue 5, 2015, pp. 472-480.
Lim, "Hyaluronic acid filler injections with a 31-gauge insulin syringe, Australasian Journal of Dermatology", vol. 51, No. 1, 2010, pp. 74-75.
Monslow et al., "Hyaluronan—a functional and structural sweet spot in the tissue microenvironment," Frontiers in Immunology, vol. 6, No. 231, 2015, 19 Pages.
Naor, "Editorial: Interaction Between Hyaluronic Acid and Its Receptors (CD44, RHAMM) Regulates the Activity of Inflammation and Cancer, Frontiers in Immunology", vol. 7, No. 39, 2016, 4 Pages.
Shu et al., "Disulfide cross-linked hyaluronan hydrogels", Biomacromolecules, vol. 3, No. 6, 2002, pp. 1304-1311.
Stern et al., "The many ways to cleave hyaluronan", Biotechnology Advances, vol. 25, No. 6, 2007, pp. 537-557.
Tokita et al., "Degradation of hyaluronic acid-Kinetic study and thermodynamics", Eur. Polym. J., vol. 32, No. 8, 1996, pp. 1011-1014.
Troncoso et al., "A kinetic study of the degradation of hyaluronic acid at high concentrations of sodium hydroxide", student thesis, 2016.
Kafedjiiski, et al., "Synthesis and in vitro evaluation of thiolated hyaluronic acid for mucoadhesive drug delivery", International Journal of Pharmaceutics, Elsevier, NL, Vo. 343, No. 1-2, Aug. 30, 2007.
International Search Report issued in PCT/EP2019/065755 mailed Sep. 19, 2019.
Vanderhooft et al., "Rheological Properties of Cross-Linked Hyaluronan-Gelatin Hydrogels for Tissue Engineering", Macromolecular Journals, (2009), p. 20-28.

* cited by examiner

A

B

C

D

HYDROGEL COMPOSITION COMPRISING A CROSSLINKED POLYMER

The present invention relates to a sterile hydrogel composition, comprising a crosslinked polymer, wherein the crosslinked polymer is an oxidation product of a thiol-modified hyaluronan, as well as uses thereof and a method for producing the same.

STATE OF THE ART

Hyaluronan, abbreviated HA, also called hyaluronic acid and its salts, e.g. sodium hyaluronate, is a naturally occurring anionic, non-sulfated glycosaminoglycan with repeating disaccharides being composed of D-glucuronic acid and N-acetyl-D-glucosamine.

High molecular weight hyaluronan is naturally present in the skin and is known for its viscoelastic properties and also for its very high propensity to absorb water. Its properties contribute to a large extent to the elasticity of the skin. Given its properties and its qualities of biocompatibility, tolerance and lack of toxicity, advantage has thus been taken of this compound for more than 10 years now in many applications in the medical and cosmetics fields, in particular aesthetic procedures. For instance, hyaluronan is used for filling wrinkles via direct injection into the dermis in the area under consideration (use as dermal filler).

Highly purified unmodified HA of biofermentative origin is perfectly biocompatible and identical to endogenous hyaluronan. However, despite having the advantage of being highly compatible with the tissues of the human body, having a high affinity for water and performing a strong moisturising function, HA does not have adequate biomechanical properties. When HA is injected into skin tissues, there is a rapid in vivo degradation by both hyaluronidases (enzymatic degradation) and free radicals (chemical degradation) present in the tissues of the human body.

Numerous solutions have been proposed to slow down the in vivo degradation of HA and to modify its chemical, physical, and biological properties, additionally providing increased resistance of the formulations to degradation during storage, to heat and therefore to sterilization.

These approaches typically involve chemical modification of HA including for example crosslinking of HA by chemical, enzymatic or photochemical means. These crosslinked hyaluronan gels can be obtained by various preparation processes. Generally, these processes require two main steps, the first consisting of hydrating hyaluronan in order to convert it into an aqueous solution (hydrogel) and the second aimed at crosslinking the HA molecules of said aqueous solution in the presence of an agent capable of inducing the crosslinking thereof (also referred to as "crosslinking agent"). Examples of crosslinking agents include formaldehyde, divinyl sulfone, biscarbodiimides, and epoxides.

For the production of dermal fillers, the crosslinking agent is most commonly chosen from epoxides, such as 1,4-butanediol diglycidyl ether (BDDE) or 1,2,7,8-diepoxyoctane (DEO), aldehydes, or poly vinylsulfones, such as divinylsulfone (DVS), and is therefore synthetic in nature.

Unfortunately, chemical modifications lead to side effects and foreign body reactions not observed with unmodified HA, which has naturally low immunogenicity and no toxicity. In the majority of marketed HA soft tissue fillers BDDE is used as a crosslinking agent. Due to the reactive nature of the epoxide groups present in BDDE, non-reacted BDDE remaining in the dermal filler might have genotoxic effects. Thus, BDDE in dermal fillers has to be maintained at trace amounts (<2 parts per million), so that expensive additional purification and test procedures are needed during production. Although the safety profile of BDDE crosslinked fillers is supported by long term clinical experience (De Boulle, Glogau et al., 2013, A review of the metabolism of 1,4-butanediol diglycidyl ether-crosslinked hyaluronic acid dermal fillers, Dermatol Surg (39): 1758-1766), BDDE may still raise some safety concerns (Choi, Yoo et al., 2015, Modulation of biomechanical properties of hyaluronic acid hydrogels by crosslinking agents, J Biomed Mater Res Part A (103A): 3072-3080).

Due to the genotoxic risks associated with BDDE, the yearly dose of dermal filler products such as Juvederm®, which may be applied over the lifetime of a patient, is limited to 20 mL per year. Administration of the commercially available dermal filler product Restylane®) is limited to a volume of 6 mL per application. Similar limitations apply to dermal fillers comprising DVS crosslinked hyaluronan.

Another problem with chemical modifications is the necessity of harsh reaction conditions, such as alkaline pH values and high temperatures (above 50° C.) to which hyaluronan has to be subjected during the crosslinking reaction in order to achieve the desired degree of crosslinking. It is known that the molecular weight of HA decreases because of hydrolytic degradation during exposure to acidic (pH below 4) or alkaline pH (pH above 10). In addition, hyaluronan is degraded at higher temperatures above 40° C. (Troncoso et al., 2016, A kinetic study of the degradation of Hyaluronic acid at high concentrations of sodium hydroxide is forth in student thesis, accessed online via uu.diva-portal.org; Stern et al., 2007. The many ways to cleave hyaluronan, Biotechnology Advances (25): 537-557; Tokita and Okamoto, 1996, Degradation of hyaluronic acid-kinetic study and thermodynamics, Eur. Polym. J. (32): 1011-1014). It is further known that low molecular weight hyaluronan fragments with a molecular weight of less than about 200 kDa have pro-inflammatory effects (Naor, 2016, Editorial: Interaction Between Hyaluronic Acid and Its Receptors (CD44, RHAMM) Regulates the Activity of Inflammation and Cancer, Frontiers in immunology 7:39; Monslow et al., 2015, Hyaluronan-a functional and structural sweet spot in the tissue microenvironment, Frontiers in immunology 6:231)

Disulfide cross-linked hyaluronan hydrogels were first described by Shu et al. (Biomacromolecules 3, 1304-1311, 2002).

The disulfide crosslinked derivative of a thiol-modified hyaluronan (HA-SH) may be obtained by a self-crosslinking mechanism. A network of crosslinked hyaluronan polymers establishes upon formation of disulfide bonds between thiol groups (HA-S-S-HA). The thiol group forming a disulfide bond may connect the pendant groups of a common HA backbone molecule or a neighbouring HA molecule, i.e. the crosslinking may be intramolecular or intermolecular, respectively. The formation of disulfide bonds from free thiol groups is an oxidation reaction that may occur spontaneously, e.g. due to ubiquitous oxygen, or upon addition of an oxidation agent.

WO 2004/037164 further studied hyaluronan modified with 3,3'-dithiobis(propanoic dihydrazide) (DTP) or 4,4'-dithiobis(butyric dihydrazide) (DTB). Gels obtained by disulfide formation and use of thiol reactive agents such as polyethylenglycol di(meth)acrylic acids for crosslinking were evaluated for their potential in tissue engineering, i.e. as a scaffold for growth and culture of cells for implantation.

In WO 2005/056608 the same techniques were employed to crosslink a thiolated hydrazide modified carboxymethyl hyaluronan to obtain macromolecular cell scaffolds. Serban et al. describe the synthesis of a 2-thioethyl ether hyaluronan derivative (Biomaterials 29, 1388-1399; 2008), which however was unsuitable for crosslinking by the investigated crosslinking agents. EP 2 103 631 describes thiol-modified macromolecules including hyaluronic acid, wherein a thiol group is introduced by a hydrazide coupling method, and its cross-linked products. The crosslinked products are either obtained with a crosslinking agent or by disulfide formation.

The synthesis of thiolated hyaluronic acid was also described in Kafedjiiski et al. (Int J Pharm 343, 48-58; 2007) as well as its potential use in drug delivery, wound healing and tissue repair. CN101367884A discloses the synthesis of HA-cysteamine conjugates which comprise both free thiol groups and disulfide groups. EP 2 614 828 describes thiol-modified biocompatible polymer derivatives with a low degree of modification and cross-linked materials thereof. WO 2008/077172 describes thiolated hyaluronic acid for tissue augmentation. In one example, WO 2008/077172 describes an intradermal application of a sterile hydrogel formulation with 2 g thiol-group containing hyaluronic acid (thiol-modified hyaluronan), wherein a depot formed by the thiol-group containing hyaluronic acid could be tactually detectable over two weeks; however, the document is silent about the specific features of the thiol-modified hyaluronan used in this example.

The inventors of the present invention further studied the potential of self-crosslinked thiol-modified hyaluronan hydrogels as soft tissue fillers.

However, initial in vivo studies with hydrogel compositions based on self-crosslinked thiol-modified hyaluronan showed faster degradation behavior after implantation in comparison to dermal fillers with an external crosslinking agent. Accordingly, it is an object of the present invention to provide a composition comprising a disulfide crosslinked polymer, wherein the disulfide crosslinked polymer is an oxidation product of a thiol-modified hyaluronan (HA-SH), which has improved properties especially regarding the application as soft tissue filler.

SHORT DESCRIPTION OF THE INVENTION

The present invention provides a sterile hydrogel composition comprising a crosslinked polymer,
wherein the crosslinked polymer is an oxidation product of a thiol-modified hyaluronan,
wherein the thiol-modified hyaluronan has a degree of modification with thiol groups of more than about 80 µmol per gram polymer, preferably more than about 105 µmol per gram polymer, more preferably more than about 120 µmol per gram polymer,
wherein the thiol-modified hyaluronan has a degree of modification with thiol groups of less than about 280 µmol per gram polymer, preferably less than about 240 per gram polymer, more preferably less than 200 µmol per gram polymer and
wherein the composition has a residual thiol content of less than 20% in respect to the degree of modification of the thiol-modified hyaluronan.

The sterile hydrogel composition according to the present invention is a hydrogel based on a modified hyaluronan with thiol groups (HA-SH), wherein the hyaluronan is cross-linked by disulfide bonds between the thiol groups of the modified hyaluronan (oxidation product of a thiol-modified hyaluronan). The oxidation product is a copolymer consisting of sections of unmodified hyaluronan and of modified hyaluronan, the latter being connected via disulfide bonds. The hydrogel is free of any additional external bifunctional crosslinking agents, such as divinyl sulfone. The hydrogel composition is characterized by comprising an oxidation product of a thiol-modified hyaluronan with an initial degree of modification between about 80 µmol thiol groups per gram polymer to about 280 µmol thiol groups per gram polymer.

The inventors found that the degree of modification of hyaluronan with thiol groups is an important feature for influencing the in vivo residence time of the sterile hydrogel. For volumizing soft tissue fillers is it desired that the volume of the implanted hydrogel (depot volume) remains constant over a period of time and thus, achieves a sustainable effect due to slow degradation. Moreover, it may be desired that the applied hydrogel shows some initial swelling after application, i.e. an increase in volume due to water uptake into the filler depot.

Studies characterizing the in vivo performance of sterile hydrogel compositions are exemplified in Examples 7 to 9 below. The depot volume in % relative to the starting point is calculated to compensate for potential differences in the application volume. The depot volume at t=0 (directly after implantation) corresponds to 100%. The depot volume may be monitored for example via magnet resonance imaging (MRI) scans. It will be understood that the depot volume as biological parameter, preferably determined in animal models, is subject to great individual variation. Accordingly individual data points are less informative and only mean values (considering multiple application sites and/or multiple study objects) give conclusive data. Of course, the performance will further depend on factors such as the tissue type at the site of implantation, the used method for measuring the depot volume and the species of the studied organism. The quantitative transferability of the data, e.g. for application in humans, may be restricted. However, results comparable to the data in rats were observed in another in vivo study with mice (data not shown). Thus, the in vivo characterisation provides a valuable tool for assessing and comparing individual hydrogel compositions against each other. Residence time may be used as a parameter to describe the presence of a mean depot volume during a period of time, preferably the presence of a depot volume of about 100% (or even greater) during a time period. A volumizing effect may be defined by a depot volume of about 100% (or greater) at a certain time point after the application of the hydrogel, for example measured in week 5 (e.g. at day 30) or preferably in week 12 (e.g. at day 81 to 84), and eventually even in week 24 (e.g. measured at 165 to 168 days) post-implantation.

Preferably, the depot volume of about 100% (or greater) is detectable during the first 12 weeks or 3 months or during the first 24 weeks or 6 months after application (residence time). The hydrogel compositions according to the invention showed a volumizing effect 12 weeks (measured at day 81 to 84) post-implantation under the exemplified study conditions. Thus, the hydrogel compositions according to invention show the desired in vivo performance promising for an applicability as soft tissue filler, e.g. in humans. Moreover, the nature of the crosslinked polymer provides a favourable toxicological safety profile and higher volumes as compared with other stabilized hyaluronan fillers may be applied (above 50 mL per application).

The most critical parameter influencing the volumizing effect of the hydrogel composition is the "degree of modification with thiol groups", which indicates the initial amount of thiol groups (typically given in µmol) per gram (g) of the thiol-modified hyaluronan and may be abbreviated as DoM. This amount of thiol groups is a characteristic of the thiol-modified hyaluronan raw material and indicates the amount of thiol groups which are available for crosslinking during the production process of the composition. Thiol groups or moieties may also be referred to as mercapto or sulfhydryl groups. Based on various examples, the inventors identified an optimal range for the degree of modification between about 80 µmol per g polymer to about 280 µmol per g polymer. On the one hand a degree of modification above 80 µmol per g polymer was necessary to produce compositions with a volumizing effect of more than 12 weeks after implantation. Surprisingly, on the other hand, using thiol-modified hyaluronan with higher degrees of modification did not result in a volumizing effect of the produced hydrogel, i.e. an increase in the depot volume (e.g. ≥335 µmol per g polymer as shown in Example 7). Without wishing to be bound by theory, it is assumed that higher degrees of modification (and consequently higher rates of crosslinking) result in a compact structure of the hydrogel that prevents incorporation of water and thereby prohibit a swelling effect. Thus, the initial degree of modification of the thiol-modified hyaluronan with thiol groups was identified as a crucial factor that influences the soft tissue filling properties of a sterile hydrogel composition. The desired volumizing effect for soft tissue filling was only obtained with compositions comprising crosslinked thiol-modified hyaluronan with an initial degree of modification in a narrow range of from 80 to 280, preferably from 100 to 240, more preferably from 120 to 200 µmol thiol groups per g polymer.

A high degree of crosslinking (via oxidation of the thiol groups) is beneficial for obtaining hydrogel compositions with elastic properties suitable for a volumizing soft tissue filler. In order to provide hydrogel compositions with reproducible and stable characteristics such as the rheological properties, the crosslinking of the thiol-modified hyaluronan (i.e. the formation of disulfide bonds) should be mostly complete before the hydrogel is further processed (i.e., undergoing further processing steps such as sieving, homogenization, filling into syringes and sterilization). However, a certain small amount of thiol groups might not be available for disulfide formation due to factors like sterical hindrance.

The sterile hydrogel composition according to the invention has a residual thiol content of less than 20% in respect to the degree of modification of the thiol-modified hyaluronan. This corresponds to more than 80% of the available thiol groups of the thiol-modified hyaluronan being oxidized during the hydrogel production process. The fraction of non-crosslinked thiol groups in the crosslinked polymer may be determined via the residual thiol content expressed in µmol per g polymer. As disclosed in example 17, high and uniform oxidation rates and thus a reproducible low residual thiol content in the sterile hydrogel composition are obtainable by use of an oxidation agent, e.g. hydrogen peroxide, during oxidizing step in the production method.

In a preferred embodiment, the hydrogel composition according to the invention has a residual thiol content of less than 15% in respect to the degree of modification of the thiol-modified hyaluronan.

Besides the degree of modification, parameters that remarkably influence the rheological and in vivo properties of the hydrogel are the concentration of the crosslinked thiol-modified hyaluronan as well as the molecular weight distribution of the hyaluronan chains.

Preferred concentrations were identified to be from about 11 mg/mL to about 20 mg/mL.

Preferably, the hydrogel composition comprises the oxidation product of the thiol-modified hyaluronan in a concentration of from about 11 mg/mL to about 20 mg/mL, more preferably of from about 13 mg/mL to about 18 mg/mL.

The concentration of the thiol-modified hyaluronan in mg/mL is given by weight in respect to the volume of the sterile hydrogel composition. The concentration preferably refers to the concentration of the salt, e.g. the sodium salt of the crosslinked thiol-modified hyaluronan. Accordingly, an equivalent amount of thiol-modified hyaluronan is provided for the preparation. Higher concentrations are not considered suitable as they result in hydrogel compositions with high viscosities without acceptable injectability. Concentrations of 9 mg/mL or lower are not considered suitable due to low elastic modulus G' observed for such hydrogel compositions. Within the range of about 14 mg/mL to about 18 mg/mL, e.g. 15 or 17 mg/mL, good rheological properties were observed.

Preferably, the thiol-modified hyaluronan has a mean molecular weight (MMW) of at least about 400 kDa, preferably at least about 500 kDa, more preferably at least about 600 kDa, such as about 700 kDa.

In another embodiment, it is preferred that the crosslinked polymer has a mean reduced post-sterilisation molecular weight of more than about 250 kDa, preferably more than about 300 kDa, more preferably more than about 350 kDa, wherein the mean reduced post-sterilisation molecular weight is defined as the mean molecular weight of a reduced thiol-modified hyaluronan from said sterile hydrogel composition after exposing said crosslinked polymer to reductive conditions. The "mean reduced post-sterilisation molecular weight" of the crosslinked polymer was identified as an additional critical factor influencing the volumizing effect of the hydrogel after implantation and will be abbreviated as MRPMW in the following. The MRPMW is determined as the molecular weight of a crosslinked thiol-modified hyaluronan (crosslinked polymer) after a preparation step, wherein the crosslinked polymer of the hydrogel composition is exposed to reductive conditions. In the hydrogel, the crosslinked polymer represents a complex network, for which a molecular weight may not be determined. Thus, it is necessary to reduce the crosslinked polymer, i.e. the crosslinking disulfide bonds are cleaved prior to determining the molecular weight. The MRPMW is a value that relates to the mean molecular weight of the polymer chains of the crosslinked polymer in the hydrogel composition. The MRPMW is defined as mean molecular weight (MMW) of a reduced thiol-modified hyaluronan from the sterile hydrogel composition, i.e. the MMW for the fraction of thiol-modified hyaluronan as determined in or obtainable from the composition post-sterilisation and post-reduction. Usually, the MRPMW determined for a thiol-modified hyaluronan from the sterile hydrogel composition is lower when compared to the mean molecular weight (MMW) of the raw material, i.e. the thiol-modified hyaluronan which is used for the production of the corresponding compositions (see Table 1). The reduction of the MRPMW in comparison to the MMW of the raw material is assumed to be the consequence of the hydrogel production procedure including sterilisation. Accordingly, using the MRPMW of the crosslinked polymer is more appropriate to characterize the hydrogel composition than using the MMW of the raw material.

However, the inventors found that when using a thiol-modified hyaluronan with a mean molecular weight (MMW) of at least about 400 kDa, preferably at least about 500 kDa, more preferably at least about 600 kDa, such as about 700 kDa, for the production of hydrogel compositions, the MRPMW of the crosslinked polymer in the hydrogel composition was about 250 kDa or higher. For example, the production procedures outlined in the examples starting with a thiol-modified hyaluronan of about 600 kDa resulted in hydrogel compositions with a MRPMW of the crosslinked polymer being in the most preferable region of about 350 kDa or higher. Vice versa, a MRPMW of about 250 kDa or higher is an evidence that the respective thiol-modified hyaluronan has a MMW being at least about 400 kDa, although the quantitative relation depends on the production procedure.

As noted, in a composition according to the invention, the MRPMW of the crosslinked polymer preferably is about 250 kDa or higher. Examples with compositions comprising a crosslinked polymer with a MRPMW below 250 kDa, e.g. 200 kDa (ID10), did not show the preferred elastic modulus G' and a mean relative depot volume above 100% over a sufficiently long time period, whereas an example composition comprising a crosslinked polymer with a MRPMW of 300 kDa showed a mean relative depot volume above 100% for 133 days. A composition comprising a crosslinked polymer with a MRPMW of 480 kDa showed a mean relative depot volume above 100% for 188 days. In particular, the MRPMW is preferably more than 300 kDa, more preferably more than about 350 kDa. According to the inventor's knowledge, the state of the art is silent about MRPMW and its role for influencing in vivo performance of a hydrogel after implantation into a soft tissue. The MRPMW is characterising the cross-linked polymer, i.e. a non-uniform network, in the hydrogel composition via a rather indirect measure. Thus, it is not surprising that the results typically show a deviation of #10% or sometimes even higher. Example 5 specifics exemplary methods of determining the MRPMW. A person skilled in the art will acknowledge that other approaches may arrive to comparable values for this parameter. For example, agarose gel electrophoresis can be used to separate different MW fractions of hyaluronan in an agarose gel using a horizontal gel chamber and a HA molecular weight ladder as marker. Stained gels are then densitometrically analyzed followed by molecular mass calculation.

On the other hand, the thiol-modified hyaluronan preferably has a mean molecular weight (MMW) of at most about 4,500 kDa, in particular at most a mean molecular weight in the range of from 4,000 kDa to 4,200 kDa. It was found that hyaluronan starting materials with even higher molecular weight specification are not available in quantity and quality necessary for preparing a thiol-modified hyaluronan suitable for preparing sterile hydrogel compositions in industrial scale and/or as dermal filler. More preferably, the thiol-modified hyaluronan has a mean molecular weight of at most 3,500 kDa or at most 2,000 kDa. For example, the mean molecular weight of the thiol-modified hyaluronan may be in the range of from about 700 kDa to about 2,000 kDa.

The invention also provides a method for producing a hydrogel composition according to the invention comprising the steps of:
a) providing a thiol-modified hyaluronan,
wherein the thiol-modified hyaluronan has a degree of modification with thiol groups of more than about 80 µmol per gram polymer, preferably more than about 105 µmol per gram polymer, more preferably more than about 120 µmol per gram polymer, and
wherein the thiol-modified hyaluronan has a degree of modification with thiol groups of less than about 280 µmol per gram polymer, preferably less than about 240 per gram polymer, more preferably less than 200 µmol per gram polymer,
in an aqueous solution,
b) oxidizing the thiol-modified hyaluronan by exposing the previously obtained aqueous solution to conditions that allow the thiol-modified hyaluronan to form a disulfide crosslinked polymer, wherein or whereby the aqueous solution becomes a hydrogel, wherein said hydrogel has a residual thiol content of less than 20% in respect to the degree of modification of the thiol-modified hyaluronan,
optionally c) adding an unmodified polymer selected from the group of biocompatible polysaccharides to the previously obtained hydrogel or to the previously obtained solution,
optionally d) sieving the previously obtained hydrogel to obtain a hydrogel with a particular particle size distribution,
e) filling the previously obtained hydrogel into a container, preferably a syringe, and exposing the filled container to conditions allowing for sterilization of the hydrogel,
f) obtaining a sterile hydrogel composition in a container comprising a crosslinked polymer.

In the method for producing a hydrogel the steps may be conducted in different sequences. Especially the steps of crosslinking (oxidizing), adding an unmodified polymer and sieving may be performed in different sequences without necessarily affecting the hydrogel quality. Preferably, the steps are conducted in the sequence a), c), b), d), e) and f), wherein the preparation of the solution (step a) and the addition of the unmodified polymer (step c) may be performed concomitantly and optionally a further component (e.g. a local anaesthetic agent) may be added at the same time.

Formation of disulfide bonds (crosslinking) naturally occurs at physiological pH values in the presence of oxygen (e.g. supplied via the surrounding air or dissolved in an aqueous solution). However, addition of an oxidation agent is preferred to ensure that the conditions in step b) are sufficient to reach the degree of oxidizing which ensures that the hydrogel has a residual thiol content of less than 20% in respect to the degree of modification of the thiol-modified hyaluronan. The active addition of a oxidizing agent accelerates and completes disulfide formation to obtain the desired low degree of residual thiol content. Moreover, adding an oxidation agent in step b) turned out to be especially relevant to ensure a reproducible and uniform result in industrial processes, i.e. including large bulk volumes.

Accordingly, in a preferred embodiment, in step b) an oxidation agent is added to the previously obtained aqueous solution.

Suitable and well established oxidizing agents are for example hydrogen peroxide (or other peroxides), ascorbic acid, dimethyl sulfoxide and hypochlorous acid (sodium hypochlorite). Under excess pressure conditions pure oxygen gas or a high oxygen gas mixture can be used to increase the concentration of oxygen available as oxidation agent in the polymer aqueous solution. The preferred amount to be added depends on the oxidation agent and the amount of thiol groups in the thiol-modified hyaluronan. Exemplarily, for hydrogen peroxide, in step b) the molar ratio of free thiol groups of thiol-modified hyaluronan to hydrogen peroxide should be preferably at most 4:1; more preferably at most 2:1.

In another aspect, the invention provides the composition according to the invention for use as medicine, in particular for use in the treatment and prevention of soft tissue conditions. Furthermore, the invention relates to the cosmetic use of the composition according to the invention. Such uses (therapeutic or cosmetic) may be referred to the use of the composition according to the invention as soft tissue filler or for tissue augmentation. Such uses preferably include the application, e.g. by injection or implantation, to a human being, while the applicability is not limited to the human species.

In another aspect, the invention relates to a method, wherein the method comprises introducing the composition according to the invention, e.g. by injection from a syringe, at a specific soft tissue site. The method relates to the use of the composition as soft tissue filler or for tissue augmentation for therapeutic as well as cosmetic purposes.

In one embodiment, uses or methods according to these aspects comprise that the hydrogel composition is introduced into a tissue site by injection from a syringe intradermally, supraperiosteally or subcutaneously into a human being.

SHORT DESCRIPTION OF THE FIGURES

The figures show:

FIG. 1: Schematic presentation of a hyaluronan-cysteamine substructure as exemplary thiol-modified hyaluronan.

Figure 2:
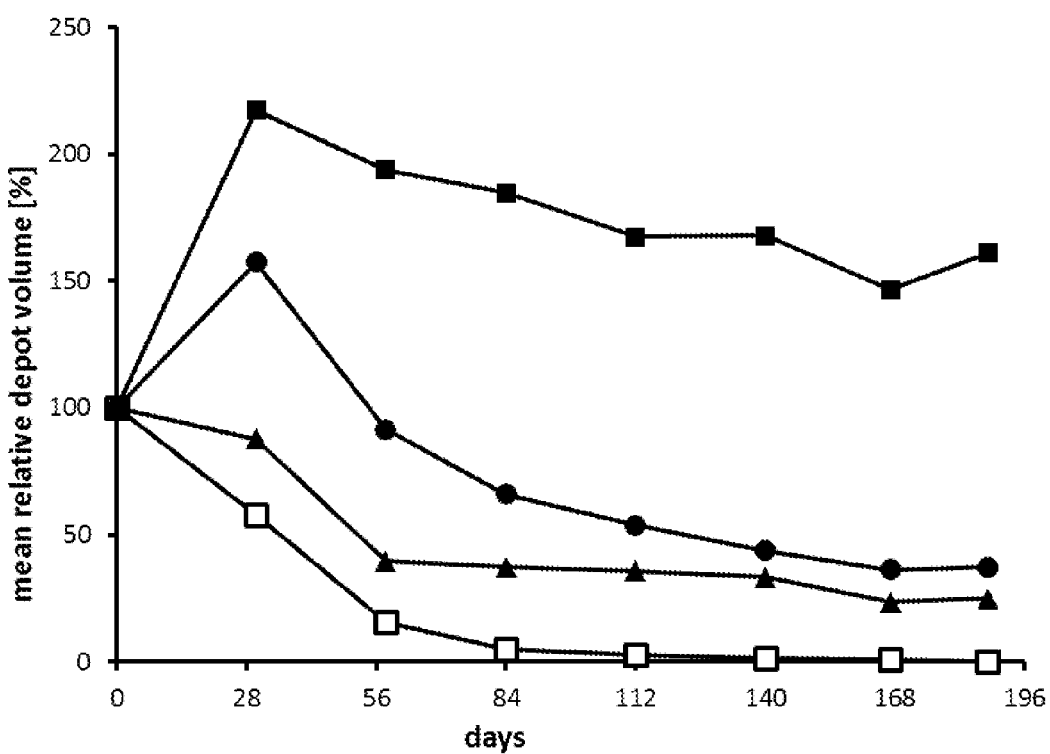

FIG. 2: In vivo performance of different hydrogel compositions as mean depot volume over time, wherein the depot volume after the implantation is indicated in respect of the initial volume at day 0 (which corresponds to 100%): composition ID 5 (full squares), composition ID 4 (empty squares), composition ID 6 (full triangles), composition ID 10 (full circles). The characteristics for the different compositions are listed in Table 1 and 2. From hydrogel compositions shown in FIG. 2, only composition ID 5 is a hydrogel composition according to the invention.

Figure 3:
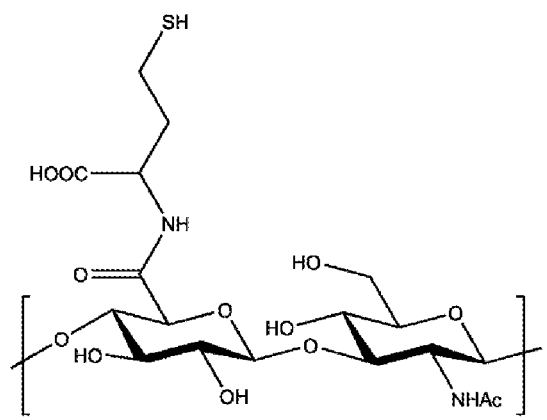
Figure 3:
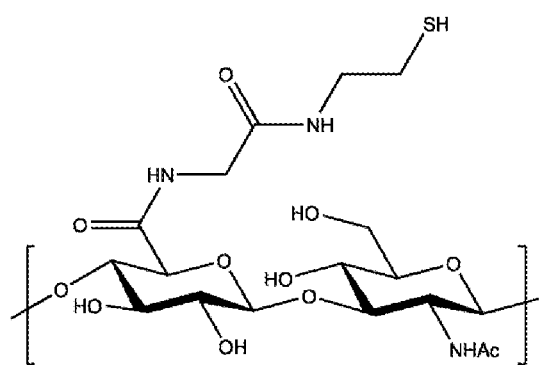
Figure 3:
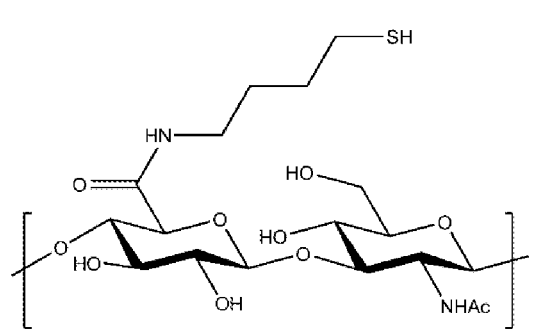
Figure 3:
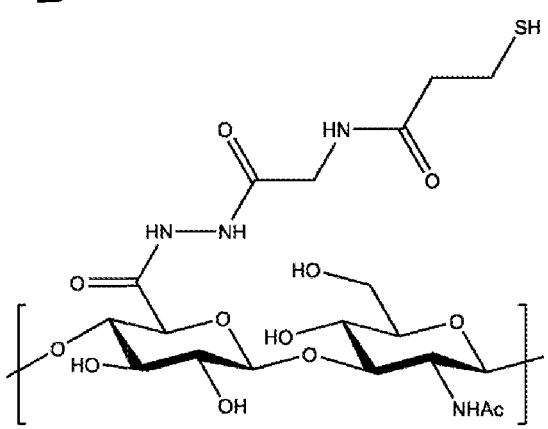

FIG. 3: Schematic presentation of further exemplary thiol-modified hyaluronans, i.e. a hyaluronan-homocysteine substructure (A), a hyaluronan-glycyl-cysteamine substructure (B), and an N-mercapto-n-butylhyaluronamide substructure (C) and a HA-DGDTPDH substructure (D).

DETAILED DESCRIPTION OF THE INVENTION

In one embodiment, the sterile hydrogel composition according to the invention preferably has an elastic modulus G' of at least about 900 Pa, preferably at least about 1,000 Pa, measured at 25° C. using a shear rate of 1 Hz.

In the context of hydrogels, the elastic modulus G' of the hydrogel composition is a typically used to characterise its elastic properties and denotes the shear storage modulus as determined with a rheometer applying shear force e.g. by rotating a (cone-)plate. Standard methods for determining the elastic modulus G' are known in the art (Stocks D., Sundaram H., Michaels J., Durrani M. J., Wortzman M. S., Nelson D. B., Rheological Evaluation of the Physical Properties of Hyaluronic Acid Dermal Fillers, 2011, *Journal of Drugs in Dermatology*, 10(9), 974-980). The elastic modulus G' is used to characterize the firmness (hardness) or softness of a gel. At the same time it is a measure for the gel's ability to resist deformation. In consequence, dermal filler hydrogels with high G' values are expected to provide better support and volumization after implantation (Stocks et al., 2011). Besides temperature and frequency of the rotating plate other variable testing conditions can influence the quantitative comparability of the elastic modulus G'. Repeated testing may typically result in a standard variation of about ±10% to the mean value e.g. 8%. In some cases it was observed that the elastic modulus varied up to 20% when the hydrogel was provided by extrusion through a needle or without needle. Thus, it is recommended stay close to the protocol as outlined below in Example 4 for assessing the elastic modulus G'.

Several hydrogel compositions according to the invention (with the degree of modification for the thiol-modified hyaluronan and optionally the concentration of the polymer as indicated) showed an elastic modulus G' of >1,000 Pa. Hydrogels with an elastic modulus of G' of less than 900 Pa did not show a mean relative depot volume above 100% over a sufficiently long time period (hydrogel composition ID 10 in Example 6), whereas a composition with an elastic modulus of 1,385 Pa (comprising a crosslinked polymer with a MRPMW of 480 kDa, hydrogel composition ID2) showed a mean relative depot volume above 100% for 188 days. Previous studies with hydrogels formed by crosslinked thiol-modified hyaluronan did not specifically focus on sterile hydrogel compositions or their suitability as soft tissue filler. Accordingly, the state of the art is silent about their elastic modulus G' and its role for influencing in vivo performance of a hydrogel based on a disulfide crosslinked polymer after implantation into a soft tissue. Moreover, data available for dermal fillers on the market (Stocks et al., 2011) show that the elastic modulus of these products, which comprise at least 20 mg/mL BDDE crosslinked hyaluronan, was in the range of about 75 Pa to about 660 Pa. Although measured under different testing conditions, these values show that the established crosslinked hyaluronan hydrogels have an elastic modulus G' well below 900 Pa or even 1,000 Pa and thus, below the preference for the present invention.

The properties of the hydrogel composition according to the invention are critically influenced by the thiol-modified hyaluronan, especially its degree of modification. Established methods for determining the degree of modification include the Ellman method or measuring the release of a chromophoric thione upon reaction of 2,2'-dithiodipyridine with thiol-bearing agent (see Example 1). Those skilled in the art will also know alternative methods resulting in similar values. Herein, the degree of modification is given in µmol of thiol groups per gram polymer. Alternatively, the degree of modification may be indicated as percentage, wherein the amount of modified repeating units is divided by the total amount of HA-repeating units in the polymer (D-glucuronic acid and N-acetyl-D-glucosamine). The degree of modification in µmol of thiol groups per gram polymer can be converted in percentage by taking into account the molecular weight of 400 g/mol of the HA-repeating unit. In this conversion, the change of molecular weight introduced by the modification is typically neglected. Accordingly, the degree of modification as specified for the thiol-modified hyaluronan in a composition according to the invention may be expressed as ranging between 3.2% and 12.0%, preferably between 4.0% or 11.2% or 4.8% and 10%.

The "thiol-modified hyaluronan" (HA-SH) is a thiol-group containing derivative of a hyaluronic acid (HA). It is characterised by the degree of modification as specified above and is accessible via known synthetic approaches starting off from hyaluronan which is available in different molecular weights (or molecular weight ranges). Numerous examples of HA modification with thiol group bearing ligands can be found in scientific and patent literature: Griesser et al. provides a review of thiolated hyaluronic acid polymers (Griesser et al., Polymers 10 (2018) 243). Acschlimann (EP 1 115 433 B1) describes a method of functionalization of HA which does not compromise the molecular weight of HA and which further provides HA molecules that are well tolerated in vivo and are biodegradable. The method is used to generate HA with different terminal functional groups for crosslinking, such as thiol groups. These side chains are introduced into HA by carbodiimide-mediated coupling of primary (protected) thiol group containing amines or disulfide-bond containing diamino or dihydrazide ligands to the carboxyl group of the glucuronic acid moiety using an active ester intermediate. Intermediate products with disulfide bonds are then reduced and intermediate products with protected thiol groups are then deprotected by removing the protecting group. Another method is described by Bulpitt et al. (U.S. Pat. No. 6,884,788) which comprises a direct reaction of the HA carboxyl group with a disulfide-bond containing carbodiimide (such as 2,2'-dithiobis(N-ethyl-(N'-ethylcarbodiimide), followed by reducing the disulfide bond with a reducing agent. WO 2008/008857 A2 discloses synthesis methods for 2-thioethyl ether derived hyaluronan. EP 0 587 715 discloses how to synthesize water insoluble anionic polysaccharides via dissolving at least one polyanionic polysaccharide (e.g., HA), in an aqueous mixture; activating the polyanionic polysaccharide with an activating agent such as a diimide, e.g. EDC or ETC, or BOP; modifying the activated polyanionic polysaccharide with a modifying compound such as 1-hydroxy-benzotriazole hydrate (HOBt) or 1-hydroxy-benzotriazole monohydrate; and reacting the activated polyanionic polysaccharide with a suitable nucleophile (such as an amino thiol) to form the desired insoluble composition. The inventors state that one major advantage of the BOP activation of polyanionic polysaccharide is that the molecular weight of the polyanionic polysaccharide is not decreased upon coupling to the nucleophile. EP 1 790 665 B1 describes a water-soluble modified hyaluronic acid, which is produced by introducing a substituent into the carboxy group of the glucuronic acid of hyaluronic acid, via an amide bond using a BOP condensing agent in an aprotic polar solvent. Diamines with a disulfide bond are among the listed substituents. Triazine-mediated amidation with DMT-MM for efficient and controlled functionalization of hyaluronic acid with cysteamine is described in Borke et al., wherein the mild reaction conditions and the minimal degradation of the polysaccharide chain are listed as advantages of using this group of coupling agents in comparison to other coupling reagents such as EDC-mediated substitution (Borke et al., Carbohydrate Polymers 116 (2015) 42-50). Liang et al. describe the introduction of thiol groups to HA via an amidation reaction of the side carboxylates with cystamine in the presence of CDMT and NMM, followed by a reducing reaction with DTT (Liang et al. Carbohydrate Polymers 132 (2015) 472-480). The thiol modification of HA with l-cysteine ethyl ester hydrochloride by means of the double catalytic system-carbodiimide/Nhydroxysuccinimide was described in Kafedjiiski et al. (Int J Pharm 343, 48-58; 2007). In WO 2004/037164 hyaluronan was modified with 3,3'-dithiobis (propanoic dihydrazide) (DTP) or 4,4'-dithiobis(butyric dihydrazide) (DTB). After reduction with a reducing agent such as DTT the corresponding thiolated HA derivatives HA-DTPH and HA-DTBH were obtained. EP 2 103 631 also describes introduction of a thiol group bearing ligand via the carboxylic groups of HA by a hydrazide coupling method. Different thiolated HA polymers (HA-DGDTPDH, HA-DPDTPDH, HA-DSCDH) were synthesized.

According to the present invention, the thiol-modified hyaluronan preferably is conjugate of a modification agent linked to hyaluronan.

Introduction of the modification agent via formation of an ester bond, amide bond or hydrazide bond between the carboxyl group of the glucuronic acid moiety of hyaluronan and the modification agent is preferred. The modification agent may comprise thiol groups in the form of disulfide bonds or as protected thiol groups during the synthesis process.

In one preferred embodiment, the modification agent is linked to the carboxyl group of the glucuronic acid moiety in the hyaluronan via an amide bond. Accordingly, the modification agent comprises at least one amino group capable to form the amide bond with the carboxyl group of the glucuronic acid moiety in the hyaluronan and the modification agent comprises a thiol group. For example, the thiol-modified hyaluronan is a hyaluronan-cysteamine conjugate, wherein cysteamine is linked to hyaluronan via an amide bond (see FIG. 1).

Similarly, other thiol group bearing modification agents may be used for the synthesis of thiol-modified hyaluronan via amide bond formation between an amino group (primary or secondary amino group, preferably primary amino group) of the modification agent and the carboxyl group of the glucuronic acid moiety in the hyaluronan.

A hyaluronan-homocysteine conjugate (FIG. 3A) was synthesized by amidation of sodium hyaluronate with homocysteine thiolactone, exploiting its unique thiol protection as thiolacton.

Free thiol groups were subsequently successfully liberated by alkaline hydrolysis in presence of a reducing agent to avoid unwanted gelling caused by disulfide formation.

Further modification agents include for example derivatives of cysteamine, cysteine or homocysteine, wherein the N-terminus of the cysteamine, cysteine or homocysteine is coupled with the carboxyl group of an amino acid. These derivatives are preferably synthesized by amidation of N-protected amino acids with cysteamine, cysteine or homocysteine, using routine peptide coupling reagents, preferably those enabling facile product purification, e.g. through removal of reactants and side products by an aqueous extraction upon reaction work up (see example 12 A—Synthesis of thiol group bearing modification agents). Alternatively, cysteamine, cysteine or homocysteine are reacted with corresponding active esters of N-protected amino acids in organic solvents, such as succinimidyl esters. A hyaluronan-glycyl-cysteamine conjugate (FIG. 3 B) is an example for the thiol-modified hyaluronan, synthesized by this approach.

A low molecular weight of the modification agent is preferred to conserve to the unique physico-chemical properties of hyaluronan as much as possible. Suitable low molecular weight modification agents to obtain a crosslinkable thiol-modified hyaluronan useful for a composition according to the invention preferably are further selected from the group comprising glutathione, cysteine, aminoalkylthiols comprising a linear or branched $C_2$-$C_6$-alkyl chain, homocysteine, carboxylate esters of homocysteine (e.g. $C_2$-$C_6$-alkyl esters of homocysteine, preferably ethyl homocysteine), and carboxylate esters of cysteine (e.g. $C_2$-$C_6$-alkyl esters of cysteine, preferably ethyl cysteine).

Aminoalkylthiol linkers can be conveniently introduced via corresponding symmetrical diamines, containing a disulfide linkage as a kind of inherent protecting group, exploited upon amide synthesis with hyaluronan. The disulfides can in turn be accessed starting from N-protected aminoalcohols: After introducing a thioester moiety, for example following Mitsunobu's protocol, saponification of the thioester under oxidative conditions delivers the desired target compounds (e.g. Example 12 C). An N-mercapto-n-butylhyaluronamide (FIG. 3 C) is an example for the thiol-modified hyaluronan synthesized by this approach.

In another preferred embodiment, the modification agent is linked to the carboxyl group of the glucuronic acid moiety in the hyaluronan via a hydrazide bond. Accordingly, the modification agent comprises at least one hydrazide group capable to form the amide bond with the carboxyl group of the glucuronic acid moiety in the hyaluronan and the modification agent comprises a thiol group. For example, the thiol-modified hyaluronan is a hyaluronan-3-mercapto-propionic acid hydrazide conjugate (HA-DTPH) or a hyaluronan-2-mercapto-ethyl-carbonyl-amino-acetic acid hydrazide conjugate (HA-DGDTPDH; see Example 12 B, FIG. 3 D).

The term "sterile" as used herein is to be understood in accordance with the art specifying a composition complying with the microbiological standards as defined for cosmetic or pharmaceutical products, for example in the United States Pharmacopoeia (USP), the European Pharmacopoeia (Ph. Eur.) or other national standards. Classically, the hyaluronan gels are sterilized after being filled into syringes. Thermal moist-heat sterilization with an autoclave is one of the standard methods, which comprises subjecting the HA gels to high-pressure saturated steam at 121° C. for around 15-20 minutes. Autoclaving for shorter time periods (for example, between about 1 minute and 5 minutes) and at higher temperatures (for example, between about 130° C. and 135° C.) might lead to a better preservation of the molecular weight of the HA molecules in the gels (see M. L. Bernuzzi, A. Giori, "An innovative way to thermally sterilize hyaluronic acid pre-filled syringes", 2016 white paper available online via www.fedegari.com, US 2016/0220729). The optimization of other autoclaving parameters (such as ensuring rapid cooling of the product) might be additionally advantageous for preserving the molecular weight of the polymer (News on sterilization of hyaluronic acid accessed online via www.steriflow.com).

The term "hydrogel" as used herein is to be understood as describing a composition which has both solid and fluid (liquid) characteristics. On one hand, the hydrogel may be injectable, i.e. it shows a fluid-like behavior. On the other hand, the hydrogel may be stiff (or rigid) enough to maintain a certain form, e.g. the hydrogel may be provided in the form of a preformed implant, thread or a filament. Thus, the term hydrogel alone does not limiting the rheological properties of the composition in a quantitative manner.

However, in a preferred embodiment, the hydrogel has an elastic modulus G' of at least about 900 Pa, preferably at least of about 1,000 Pa, measured at 25° C. using a rheometer with a shear rate of 1 Hz. The hydrogel's elastic modulus G' is directly influenced by the factors
- degree of crosslinking (being defined by the critical degree of modification, i.e. a characteristic according to the present invention),
- the concentration of the crosslinked polymer, and
- the MRPMW (being dependent on the mean molecular weight of the thiol-modified hyaluronan).

The exemplary section provide various compositions, which guide the person skilled in the art to vary these factors in order to obtain the desired elastic modulus G' of at least about 1,000 Pa. It is understood that a low concentration could be compensated with higher molecular weight and vice versa. However, the preferences for the concentration of the crosslinked polymer and the MPRMW provide a clear guidance how the person skilled in the art can obtain a hydrogel with the preferred elastic modulus of at least about 1,000 Pa. The clastic modulus G' represents a valuable parameter to characterized the hydrogels according to the invention which can be verified based on the final hydrogel without elaborated technical efforts.

In a preferred embodiment, the composition further comprises an unmodified polymer selected from the group of biocompatible polysaccharides. Preferably, the unmodified polysaccharide is unmodified hyaluronan (HA). The unmodified (non-crosslinked) or also referred to as free hyaluronan can complement the hydrogel composition. Unmodified HA is commonly added as a lubricant to soft tissue fillers to ensure easy injectability by decreasing the extrusion force required to inject the products through a needle or cannula. Preferably, the free hyaluronan raw material used for the production of the composition has a molecular weight in the range of about 500 kDa to about 3,500 kDa. However, due to the fast degradation of unstabilized hyaluronan, the person skilled in the art will understand that the in vivo performance of the composition as soft tissue filler is largely driven by the crosslinked polymer and the properties of the underlying thiol-modified hyaluronan. It is preferred that the unmodified polysaccharide is comprised in a concentration lower than the crosslinked polymer. Exemplarily, an unmodified hyaluronan is comprised in the compositions at concentrations of 3 mg/mL to 7 mg/mL, such as 5 mg/mL, wherein the concentration preferably refers to the concentration of a salt, e.g. sodium hyaluronate.

The hydrogel composition may include a local anaesthetic agent and/or one or more components selected from a variety of other components, such as, growth factors, vitamins, polyalcohols, alkali metal halides, minerals, antioxidants, amino acids, coenzymes, ceramic particles (such as calcium hydroxyl apatite particles), polymeric particles, polymers (such as polyethylene glycol, glycosaminoglycans, lubricins, polysaccharides, and their derivatives), proteins (such as elastin, collagen, keratin, silk fibroin), anti-cellulite agents, anti-scarring agents, anti-inflammatory agents, anti-irritant agents, vasoconstrictors, anti-hemorrhagic agents (such as hemostatic agents and anti-fibrinolytic agents), tensioning agents, anti-acne agents, pigmentation agents, anti-pigmentation agents, anti-phlogistic agents, anti-rheumatic agents, anti-viral agents, anti-infective agents, anti-septic agents, chemotherapeutic agents, cytostatic agents, anti-allergic agents, anti-varicosic agents, analgesics, antibiotics, antimycotics, spasmolytics, antihistamines, agents for treating hemorrhoids, therapeutic agents for treating the skin, and moisturizing agents.

The addition of a local anaesthetic agent to the hydrogel composition is particularly desirable in view of its ability to mitigate pain upon injection. Preferably, the anaesthetic agent is lidocaine, such as in the form of an acid addition salt, e.g. lidocaine HCl.

In a method for producing the hydrogel a local anaesthetic agent and/or one or more components may be added during different production steps, i.e. in one embodiment the local anaesthetic agent and/or one or more components is/are added during optional step c) or in another embodiment independently from adding the unmodified polymer e.g. added to the solution during step a) or to the hydrogel obtained in step c) or d). In a preferred embodiment an anaesthetic agent, e.g. lidocaine HCl, is added during step a) or during step c). In an embodiment, wherein step c) precedes step b), i.e. wherein an unmodified hyaluronan is added prior to crosslinking, it is preferred that also a local anaesthetic agent and/or one or more further components are included prior to the crosslinking step.

Furthermore, it will be understood that a main component of the hydrogel composition is water. Preferably water for injection or purified water is used for producing the composition. Besides, it will be acknowledged that the composition may be buffered to exhibit a physiologically acceptable pH in the range of 6.7 to 7.8. Suitable buffers are known to those skilled in the art and include for example phosphate buffer. The composition also exhibits a physiologically-acceptable osmolality, which is similar to the normal osmolality of extracellular fluid in the subject to be treated (e.g. in humans). Thus, the composition may have an osmolality in the range of 250-350 mOsmol/kg and may include additional solutes to adjust the osmolality, such as sodium chloride, calcium chloride, and/or potassium chloride.

The hydrogel composition is sterile and may be used (in a method), wherein the hydrogel composition is a medicine, a cosmetic or medical device. The hydrogel is implanted, preferably by injection through a needle or cannula, at a site of application, preferably a soft tissue. Alternatively, the hydrogel may be implanted via a surgical procedure. Once applied the hydrogel may be referred to as (hydrogel) implant or depot. The hydrogel composition according to the invention is biocompatible and forms an absorbable (i.e. biodegradable) implant. Thus, the hydrogel composition according to the invention is usable as soft tissue filler. The characteristic hydrogel composition according to the invention did show good tolerability and an in vivo volumizing effect after implantation to a soft tissue in rats and mice. These studies support that the hydrogel is a valuable soft tissue filler for various applications.

Soft tissue fillers comprising biomaterials such as stabilized hyaluronan are delivered to the tissue site, where augmentation is desired by means of an injectable hydrogel composition. The aims of the uses or methods referring to soft tissue filling include to augment soft (dermal) tissue, to correct congenital anomalies, acquired defects or cosmetic defects.

The main effect of the hydrogel composition is purely physical as it has a filling effect based on the original volume and the swelling of the implant. Thus, in absence of any physiological or pharmacological interaction, the use may be classified as cosmetic and the composition may be considered as a cosmetic or medical device. Applications, wherein the use of the hydrogel composition according to the invention may be considered as cosmetic include for example the reduction of signs of age, e.g.

application into the tissue of the vulva and vagina for nonsurgical female genital rejuvenation purposes application into the dermis, subdermal or supraperiosteal application.

Exemplarily, the hydrogel composition may be used (in a method) for cosmetic purposes, e.g. for filling wrinkles, for treating skin defects, for restoring lost volume of the face or the body (e.g. breast, ear lobe), for reducing dimples in cellulitis, for treating tear trough deformities, for shaping the contours of the face or the body (e.g. buttock enhancement, hip augmentation, calf augmentation), for penis enlargement (penile girth enhancement, glans penis augmentation).

In other cases the filling and augmentation of a soft tissue may result in a treatment or prevention of a disease, i.e. wherein symptoms of the disease are reduced, alleviated and/or prevented from (re-)occurrence. Disease that are caused by a soft tissue defect may benefit from the temporary and/or local structural filling, damping, support or augmentation of the surrounding tissue by the applied hydrogel. Diseases, wherein the hydrogel composition may be used for treatment or prevention include for example metatarsalgia, a pain disease of the fatty pad of the ball of the foot, for which use the hydrogel composition according to the invention may be applied at the fatty pad of the ball of the foot soft tissue, urinary or fecal incontinence, for which indications the hydrogel composition according to the invention may be applied at the tissue defining sphincters, vulvovaginal atrophy (also genito-urinary syndrome of menopause), for which indication the hydrogel composition according to the invention may be applied at the vulvovaginal area via injection into the vaginal mucosa and the vestibule and/or for labia majora augmentation, wherein a reconstruction of the labia majora will ensure a close contact between both labia majora to protect the inner structures of the vulva vocal cord impairment, venous valve insufficiency, or facial lipoatrophy, debilitating scars or morphological asymmetry or deformation (congenital or resulting as consequence of trauma or surgery, e.g. of the thorax or of the face), for which indications the hydrogel is applied for reconstructive purposes.

EXAMPLES

Example 1—Determination of Degree of Modification

Quantification of thiol groups in a thiol-modified hyaluronan (HA-SH) used as raw material for preparation of hydrogel compositions is based on a wet chemistry method employing 2,2'-dithiodipyridine (DTDP). Free thiol moieties which are covalently bound to a polymeric backbone undergo thiol-disulfide exchange reaction with DTDP, whereas one equivalent of a chromophoric thione is released. In buffered acidic medium (pH=4), the absorption of the resulting thione can be measured photometrically at 343 nm.

About 420 mg of thiol-modified hyaluronan were accurately weighed and dissolved in 30 g of 0.01 N HCl under continuous magnetic stirring for 2-3 hours to prepare a stock solution. Then, about 310 mg of the stock solution were accurately weighed and mixed with 4200 mg acetate buffer pH 4 in an eppendorf tube to prepare a sample solution. Three sample solutions were prepared from each stock solution. 25.0 mg N-acetylcysteine were accurately weighed and solved in 25.0 mL of acetate buffer (pH 4). This solution was then further diluted with acetate buffer (pH 4) for the preparation of a calibration curve. Acetate puffer was used for the blank value. 500 µL of a solution containing 0.125 mg/mL of DTDP in acetate buffer (pH 4) were added to 500 µL of each sample solution (calibration curve, sample solution and blank value). The solutions were briefly homogenized and incubated for 30 min at room temperature. Finally, each sample (calibration curve, sample solution and blank value) was transferred into a microcuvettes and measured at 342 nm in a spectrophotometer against the blank value.

Example 2—Determination of Residual Thiol Content

For the determination of the residual thiol content of the crosslinked polymer in the hydrogel composition (i.e. the HA-SH polymer after crosslinking and production of the compositions) a similar method as described above was used.

About 50 mg of each sample hydrogel were accurately weighed and mixed with 1.3 mL of a solution containing 0.125 mg/mL of DTDP in acetate buffer (pH 4). 25.0 mg N-acetylcysteine were accurately weighed and solved in 200.0 mL of acetate buffer (pH 4). This solution was then further diluted with acetate buffer (pH 4) for the preparation of a calibration curve. Acetate puffer was used for the blank value. 500 µL of a solution containing 0.125 mg/ml of DTDP in acetate buffer (pH 4) were added to 500 µL of each sample of the calibration curve and the blank. All samples were incubated under continuous agitation for 120 min at room temperature. After centrifugation of all samples 500 µL of each supernatant were further diluted with 500 µL acetate buffer and measured at 342 nm in a spectrophotometer against the blank value.

Example 3—Methods of Producing a Hydrogel

Method A

Dissolution: thiol-modified hyaluronan, unmodified hyaluronan, and lidocaine HCl are concomitantly dissolved in an aqueous solution Crosslinking: After adjustment of the pH to about 6.8 to 7.6 thiol-modified hyaluronan is crosslinked via the oxidation of thiol groups to disulfide bridges by oxygen Sieving: Optionally the hydrogel comprising crosslinked thiol-modified hyaluronan, unmodified hyaluronan and lidocaine HCl is pressed through a filter plate with a defined mesh size (once or multiple times)

Sterilization: Autoclavation after filling of the hydrogel into syringes

Method B

Dissolution: Thiol-modified hyaluronan, unmodified hyaluronan, and lidocaine HCl are concomitantly dissolved in an acidic aqueous solution.

Crosslinking: After adjustment of the pH to about 6.8 to 7.6 thiol-modified hyaluronan is crosslinked via the oxidation of thiol groups to disulfide bridges by an oxidation agent and oxygen.

Sieving: Optionally the hydrogel comprising crosslinked thiol-modified hyaluronan, unmodified hyaluronan and lidocaine HCl is pressed through a filter plate with a defined mesh size (once or multiple times).

Sterilization: Autoclavation after filling of the hydrogel into syringes

Method C

Dissolution: Thiol-modified hyaluronan is dissolved in an aqueous solution; a separate solution comprising unmodified hyaluronan and lidocaine HCl in phosphate buffer (pH 6.8-7.6) is prepared.

Crosslinking: After adjustment of the pH to about 6.8 to 7.6 thiol-modified hyaluronan is crosslinked via the oxidation of thiol groups to disulfide bridges by oxygen.

Sieving: The hydrogel comprising crosslinked thiol-modified hyaluronan is pressed through a filter plate with a defined mesh size (once or multiple times).

Homogenization: The hydrogel comprising crosslinked thiol-modified hyaluronan and the solution comprising unmodified hyaluronan and lidocaine HCl are homogenized and optionally pressed through a filter plate with a defined mesh size (once or multiple times).

Sterilization: Autoclavation after filling of the hydrogel into syringes

Method D

Dissolution: Thiol-modified hyaluronan is dissolved in an aqueous solution; a separate solution comprising unmodified hyaluronan and) lidocaine HCl in phosphate buffer (pH 6.8-7.6) is prepared.

Crosslinking: After adjustment of the pH to about 6.8 to 7.6 thiol-modified hyaluronan is crosslinked via the oxidation of thiol groups to disulfide bridges by an oxidation agent and oxygen.

Sieving: The hydrogel comprising crosslinked thiol-modified hyaluronan is pressed through a filter plate with a defined mesh size (once or multiple times).

Homogenization: The hydrogel comprising crosslinked thiol-modified hyaluronan and the solution comprising unmodified hyaluronan and lidocaine HCl are homogenized and optionally pressed through a filter plate with a defined mesh size (once or multiple times).

Sterilization: Autoclavation after filling of the hydrogel into syringes

Method E

Dissolution: Thiol-modified hyaluronan and lidocaine HCl are dissolved in an aqueous solution; a separate solution comprising unmodified hyaluronan in phosphate buffer (pH 6.8-7.6) is prepared.

Crosslinking: After adjustment of the pH to about 6.8 to 7.6 thiol-modified hyaluronan is crosslinked via the oxidation of thiol groups to disulfide bridges by oxygen.

Sieving: The hydrogel comprising crosslinked thiol-modified hyaluronan and lidocaine HCl is pressed through a filter plate with a defined mesh size (once or multiple times).

Homogenization: The hydrogel comprising crosslinked thiol-modified hyaluronan and lidocaine HCl and the solution comprising unmodified hyaluronan are homogenized and optionally pressed through a filter plate with a defined mesh size (once or multiple times).

Sterilization: Autoclavation after filling of the hydrogel into syringes.

Method F

Dissolution: Thiol-modified hyaluronan and lidocaine HCl are dissolved in an acidic aqueous solution; a separate solution comprising unmodified hyaluronan in phosphate buffer (pH 6.8-7.6) is prepared.

Crosslinking: After adjustment of the pH to about 6.8 to 7.6 thiol-modified hyaluronan is crosslinked via the oxidation of thiol groups to disulfide bridges by an oxidation agent and oxygen.

Sieving: The hydrogel comprising crosslinked thiol-modified hyaluronan and lidocaine HCl is pressed through a filter plate with a defined mesh size (once or multiple times).

Homogenization: The hydrogel comprising crosslinked thiol-modified hyaluronan and lidocaine HCl and the solution comprising unmodified hyaluronan are homogenized and optionally pressed through a filter plate with a defined mesh size (once or multiple times).

Sterilization: Autoclavation after filling of the hydrogel into syringes.

Method G

Dissolution: Thiol-modified hyaluronan, unmodified hyaluronan, and lidocaine HCl are consecutively dissolved in an aqueous solution.

Crosslinking: After adjustment of the pH to about 6.8 to 7.6 thiol-modified hyaluronan is crosslinked via the oxidation of thiol groups to disulfide bridges by oxygen.

Sieving: Optionally the hydrogel comprising crosslinked thiol-modified hyaluronan, unmodified hyaluronan and lidocaine HCl is pressed through a filter plate with a defined mesh size (once or multiple times).

Sterilization: Autoclavation after filling of the hydrogel into syringes.

Method H

Dissolution: Thiol-modified hyaluronan, unmodified hyaluronan, and lidocaine HCl are consecutively dissolved in an acidic aqueous solution.

Crosslinking: After adjustment of the pH to about 6.8 to 7.6 thiol-modified hyaluronan is crosslinked via the oxidation of thiol groups to disulfide bridges by an oxidation agent and oxygen.

Sieving: Optionally the hydrogel comprising crosslinked thiol-modified hyaluronan, unmodified hyaluronan and lidocaine HCl is pressed through a filter plate with a defined mesh size (once or multiple times).

Sterilization: Autoclavation after filling of the hydrogel into syringes.

Method I

Dissolution solution 1: Thiol-modified hyaluronan, unmodified hyaluronan and lidocaine HCl are concomitantly dissolved in water.

Crosslinking solution 1: After adjustment of the pH to about 6.8 to 7.6 thiol-modified hyaluronan is crosslinked via the oxidation of thiol groups to disulfide bridges by an oxidation agent and oxygen.

Dissolution solution 2: Thiol-modified hyaluronan, unmodified hyaluronan and optionally lidocaine HCl are concomitantly dissolved in water.

Crosslinking: The pH of solution 2 is adjusted to about 6.8 to 7.6, immediately followed by mixing equal parts of the crosslinked solution 1 with solution 2. Thiol-modified hyaluronan is crosslinked via the oxidation of thiol groups to disulfide bridges by an oxidation agent and oxygen.

Sieving: Optionally the hydrogel comprising crosslinked thiol-modified hyaluronan, unmodified hyaluronan and lidocaine HCl is pressed through a filter plate with a defined mesh size (once or multiple times).

Sterilization: Autoclavation after filling of the hydrogel into syringes.

Method J

Dissolution: Thiol-modified hyaluronan and unmodified hyaluronan are dissolved in an aqueous solution; a separate solution comprising lidocaine HCl is prepared.

Crosslinking: After adjustment of the pH to about 6.7 to 7.8 thiol-modified hyaluronan is crosslinked via the oxidation of thiol groups to disulfide bridges by oxygen.

Sieving: The hydrogel comprising crosslinked thiol-modified hyaluronan and unmodified hyaluronan is pressed through a filter plate with a defined mesh size (once or multiple times).

Homogenization: The hydrogel comprising crosslinked thiol-modified hyaluronan and unmodified hyaluronan and the solution comprising lidocaine HCl are homogenized and optionally pressed through a filter plate with a defined mesh size (once or multiple times).

Sterilization: Autoclavation after filling of the hydrogel into syringes.

Method K

Dissolution: Thiol-modified hyaluronan and unmodified hyaluronan are dissolved in an aqueous solution; a separate solution comprising lidocaine HCl is prepared.

Crosslinking: After adjustment of the pH to about 6.7 to 7.8 thiol-modified hyaluronan is crosslinked via the oxidation of thiol groups to disulfide bridges by an oxidation agent and oxygen.

Sieving: The hydrogel comprising crosslinked thiol-modified hyaluronan and unmodified hyaluronan is pressed through a filter plate with a defined mesh size (once or multiple times).

Homogenization: The hydrogel comprising crosslinked thiol-modified hyaluronan and unmodified hyaluronan and the solution comprising lidocaine HCl are homogenized and optionally pressed through a filter plate with a defined mesh size (once or multiple times).

Sterilization: Autoclavation after filling of the hydrogel into syringes.

Example 4—Determination of Clastic Modulus G'

Oscillatory rheological measurements of all compositions were performed using an Anton Paar MCR 102 Rheometer with a cone-plate system. The compositions were transferred to the rheometer via injection through a 27G needle (or without needle, where indicated). The clastic modulus was obtained during a frequency test with constant deformation within the linear viscoelastic region of the hydrogel at a temperature of 25° C. and a frequency of 1 Hz.

Example 5—Determination of Molecular Weight

A Viscotek TDAmax temperature controlled, multi-detector SEC system comprising high sensitivity detectors in series—Photodiode Array UV, Light Scattering (both RALS and LALS), Refractive Index and Viscometer was used for the measurements. The refractive index detector recorded the concentration of the sample resulting in the respective distribution curve. In combination with the light scattering detectors, the molecular weight (MW) was determined. For size exclusion chromatography (SEC) analysis, samples were diluted with PBS resulting in a final polymer concentration of 0.1 mg/mL.

Errors or fluctuations which occur during this test typically result in a deviation of about 10%.

Samples for determination of the mean reduced post-sterilisation molecular weight (MRPMW) were prepared by dispersing about 200 mg of the sterile investigated hydrogel composition in 1.8 mL phosphate buffered saline (PBS) and incubation for 2 hours at room temperature. Crosslinked thiol-modified hyaluronan was separated from free hyaluronan via centrifugation. The precipitate was redispersed in PBS. After repetitive extraction/centrifugation steps, the residual gel was treated with a reducing agent (TCEP·HCl (tris(2-carboxyethyl)phosphine hydrochloride)) for 3 hours to cleave disulfide bridges followed by the acidification of the resulting solution with 5 N HCl (reduction). The reduced thiol-modified hyaluronan was precipitated with ethanol and recovered by centrifugation (a thiol-modified hyaluronan from the sterile hydrogel composition). The precipitate was dissolved in 4 mL of an aqueous solution containing a capping agent for free thiol moieties (2-(2-aminoethyldisulfanyl)pyridine-3-carboxylic acid) in a concentration of 2 mg/mL. After 3 h incubation at room temperature the sample was further diluted with PBS.

Alternatively, the MRPMW of the crosslinked polymer was determined by a subtraction method. Both approaches result in similar values. After sterilization of a hydrogel composition comprising crosslinked polymer and free hyaluronan a reducing agent was added to the hydrogel to quantitatively break disulfide bonds. The MW distribution of thiol-modified hyaluronan in its reduced form and free hyaluronan was then determined simultaneously ($M_w$(total)). In addition, the MW of free hyaluronan was determined: 200 mg of the sterile investigated hydrogel composition were dispersed in 1.8 mL phosphate buffered saline (PBS) and incubated for 2 hours at room temperature. After centrifugation the supernatant was used for SEC analysis of the MW of free hyaluronan ($M_W$(HA)).

By determining the molecular weight of the free hyaluronan ($M_W$(HA)) and the combined molecular weight of the free hyaluronan and reduced thiol-modified hyaluronan ($M_W$ (total)), the MRPMW (here $M_W$(HA-SH)) can be calculated according to equation (I), wherein $C_{HA}$ and $C_{HA-SH}$ represent the fraction of free hyaluronan and reduced thiol-modified hyaluronan, respectively:

$$M_W(HA-SH) = \frac{M_W(\text{total}) - M_W(HA)\frac{C_{HA}}{C_{HA}+C_{HA-SH}}}{\frac{C_{HA-SH}}{C_{HA}+C_{HA-SH}}} \quad (I)$$

Comparative results are given in Table 1 with the corresponding mean molecular weight (MMW) of the HA-SH raw material used for hydrogel production. Typically, the MRPMW is lower than the MMW. The production of the hydrogel composition influences the molecular weight distribution.

Example 6—Formulation of Compositions

Various sterile hydrogel compositions are listed in Table 1, wherein the main difference between the compositions lies in the characteristics of the crosslinked polymer, which is an oxidation product of thiol-modified hyaluronan (HA-cysteamine). Hydrogels comprising 17 mg/mL crosslinked HA-cysteamine, 5 mg/mL unmodified sodium hyaluronate and 3 mg/mL lidocaine HCl were produced in a similar method (compare methods B and H above). The MMW and the degree of modification (DoM) as properties of the thiol-modified hyaluronan (HA-SH) raw material as well as the MRPMW, the elastic modulus G' and the residual thiol content as properties of the crosslinked polymer were determined as described above.

The formation of disulfide bonds was monitored via measuring residual thiol content of the crosslinked polymers and comparison with the initial degree of modification of the thiol-modified hyaluronan polymer raw materials. It was found that in all 10 compositions more than 98% of the initially available thiol groups of the polymer were oxidized during production.

Both, the MRPMW of the crosslinked polymer and the initial degree of modification with thiol groups of the thiol-modified hyaluronan raw material influenced the elastic properties of the hydrogels with the same concentration of crosslinked hyaluronan. Using thiol-modified hyaluronan polymers with a higher degree of modification for the production of the hydrogel compositions resulted in higher rates of crosslinking as clearly evidenced by increased elastic properties of the hydrogels. When comparing hydrogel compositions prepared with thiol-modified hyaluronan with a medium degree of modification with thiol groups in the range of 119 µmol to 150 µmol per gram polymer (hydrogel compositions ID2, ID5, ID8 and ID10) the influence of the MRPMW on the elastic properties of the hydrogels is clearly evident. The elastic modulus of hydrogel compositions ID2, ID5 and ID8 was above 1,000 Pa. The same effect was observed when comparing hydrogel compositions prepared with thiol-modified hyaluronan with a low degree of modification (hydrogel compositions ID1*, ID4* and ID7*). For hydrogel compositions prepared with thiol-modified hyaluronan with a high degree of modification (hydrogel compositions ID3*, ID6* and ID9*) the influence on the polymer MRPMW on the elastic properties was less pronounced.

Example 7—In Vivo Characterization of Implanted Hydrogel Compositions

Various compositions according to the invention as well as comparative compositions were investigated for the development of the mean depot volume over time after implantation via injection. Ten different compositions of hydrogels summarized in Table 1 were tested.

The compositions were injected intradermally into the back skin of female Sprague Dawley rats using 16 testing animals with an average of 12 applications per composition. Eight depots were applied per rat. 50 µL of the respective composition was injected per depot using a 25 G needle and the volume of the generated depots was monitored by MRI (Siemens Espree 1.5 T MRT device) at distinct time points for a total time period of 188 days.

TABLE 1

List of 10 sterile hydrogel compositions each comprising a different crosslinked polymer

| ID | MMW HA-SH raw material [kDa] Mean | S.D. | MRPMW oxidized HA-SH [kDa] Mean | S.D. | DoM HA-SH raw material [µmol/g] Mean | residual thiol content [µmol/g] Mean | Elastic modulus G' [mPa] Mean | S.D. |
|---|---|---|---|---|---|---|---|---|
| 1* | 576 | 24 | 430 | 28 | 48 | 0.26 | 663,438 | 20,446 |
| 2 | 628 | 8 | 480 | 10 | 119 | 0.88 | 1,384,803 | 25,982 |
| 3* | 547 | 5 | 520 | 42 | 335 | 5.92 | 2,172,653 | 185,608 |
| 4* | 1201 | 15 | 610 | 16 | 43 | 0.32 | 714,068 | 41,655 |
| 5 | 1335 | 18 | 710 | 70 | 130 | 1.06 | 1,543,920 | 59,579 |
| 6* | 957 | 13 | 560 | 19 | 350 | 4.4 | 2,408,693 | 117,637 |
| 7* | 1614 | 15 | 1000 | 40 | 51 | 0.50 | 1,126,583 | 41,929 |
| 8 | 1625 | 25 | 937 | 92 | 141 | 1.48 | 2,045,747 | 163,765 |
| 9* | 1177 | 25 | 680 | 5 | 367 | 3.99 | 2,224,367 | 13,824 |
| 10 | 277 | 12 | 200 | 20 | 150 | 0 | 896,276 | n.d. |

An asterisk (*) indicates those examples that do not fall under the scope of the claims but are included for comparison.
S.D. abbreviates standard deviation.

Individual hydrogel depot volumes (mm³) were calculated according to MRI scans and monitored over time. Calculated volumes were normalized to results obtained at day 0 (immediately after application) and are indicated in percent (%). FIG. 2 shows the development of the depot volume for four exemplary compositions. The mean relative depot volumes at day 84 and day 188 of different compositions are listed in Table 2 for all 10 compositions.

TABLE 2

Mean relative depot volume measured on day 84 and day 188 in percent.

| ID | Mean relative depot volume [%] at day 84 | Mean relative depot volume [%] at day 188 |
|---|---|---|
| 1* | 0.0 | 0.0 |
| 2 | 151.5 | 110.3 |
| 3* | 51.9 | 48.1 |
| 4* | 5.0 | 0.0 |
| 5 | 184.7 | 160.9 |
| 6* | 37.2 | 24.8 |
| 7* | 41.4 | 18.0 |
| 8 | 165.9 | 136.1 |
| 9* | 51.5 | 37.6 |
| 10 | 65.9 | 37.3 |

An asterisk (*) indicates those examples that do not fall under the scope of the claims but are included for comparison.

With the exception of two compositions comprising crosslinked thiol-modified hyaluronan with an initial degree of modification below 50 µmol thiol groups per gram polymer (hydrogel compositions ID 1* and ID 4*), all hydrogel depots were detected at least for 6 months. However, only three compositions comprising a crosslinked thiol-modified hyaluronan with a medium degree of thiol modification (hydrogel compositions ID 2, ID 5 and ID 8) and an elastic modulus of more than 1,000 Pa (a MPRMW of more than 200 kDa) showed a volumizing effect during 6 months study duration. The depot volumes of all other compositions were decreased by 50% and more during this time frame.

Example 8—Formulation and Characterisation of Hydrogel Compositions ID11 to ID15 Comprising a Crosslinked Thiol-Modified Hyaluronan with a DoM of 151 µmol Per g Polymer A sterile hydrogel composition comprising 17.9 mg/mL crosslinked HA-cysteamine sodium salt, 3 mg/mL lidocaine HCl and 5 mg/mL unmodified sodium hyaluronate was produced according to method G. In brief, 3580 mg HA-cysteamine sodium salt (dry weight, MMW 730 kDa, degree of modification 151 µmol/g polymer), 600 mg lidocaine HCl (dry weight) and 1160 mg NaCl were dissolved in 185 g water for injection under mechanical stirring at room temperature for about 3 hours. 1000 mg sodium hyaluronate (dry weight, MW 2400 kDa) were then added to the solution under continued stirring at room temperature for about another 3 hours. Phosphate buffer pH 11 was then added to a final amount of 200 g composition. The solution was homogenized for about 15 min. After incubation overnight at room temperature the now crosslinked hydrogel was pressed through a filter plate with a mesh size of 200 µm. The hydrogel was then filled into 1 mL glass syringes and sterilized via autoclavation (121° C./15 min). The elastic modulus was determined in analogy to Example 4. The hydrogel was applied to the rheometer directly from the syringe (without needle attachment) and G' was determined to be 1,619±143 Pa. The sterile hydrogel had a pH of 7.34 and an osmolality of 337 mOsmol/kg (hydrogel ID11).

Degree of modification (DoM), MRPMW, and residual thiol content were determined as described above and are summarized in Table 3.

TABLE 3

Characteristics of a hydrogel composition

| ID | MMW HA-SH raw material [kDa] Mean | MRPMW oxidized HA-SH [kDa] Mean | DoM HA-SH raw material [µmol/g] Mean | residual thiol content [µmol/g] Mean | Elastic modulus G' [mPa] Mean (S.D.) | Production method | pH |
|---|---|---|---|---|---|---|---|
| 11 | 730 | 406 | 151 | 17 | 1,619,000 (143,000) | A (sieving) | 7.34 |
| 12 | 730 | 528 | 151 | 2 | 1,965,900 | A (no sieving) | 7.66 |
| 13 | 730 | 595 | 151 | n.d. | 1,536,200 | B (no sieving) | 7.08 |
| 14 | 730 | n.d. | 151 | n.d. | 1,713,567 | A (sieving) | 7.70 |
| 15 | 730 | 430 | 151 | 12 | 1,532,167 | E (sieving) | 7.39 |

The abbreviation S.D. stands for standard deviation.

The same thiol-modified hyaluronan (MMW 730 kDa, degree of modification 151 µmol/g polymer) was used to produce four sterile hydrogel compositions comprising 17.9 mg/mL crosslinked HA-cysteamine sodium salt, 3 mg/mL lidocaine HCl and 5 mg/mL unmodified sodium hyaluronate according to method A (without sieving), method A (with sieving), method B (without sieving) and method E (with sieving), respectively, as described in example 4.

All compositions had an osmolality in the range of from 270 to 330 mOsmol/kg and a physiologically acceptable pH (see Table 4). The elastic modulus G' of the compositions (determined after injection through a 27G needle), the MRPMW and the residual thiol content of crosslinked polymer in the hydrogel were determined as described above. Residual thiol group content and MRPMW of the crosslinked polymer in composition ID14 were not determined. Composition ID12 and ID14 were produced from the same hydrogel batch, the only difference being the sieving step. Since sieving is not expected to influence MRPMW and residual thiol content of the crosslinked polymer identical values as obtained with composition ID12 may be assumed for composition ID14. The results are listed in Table 4.

These compositions were tested in vivo similarly to the test-set up described in example 7 with 12 intradermal applications per composition. All compositions had a volumizing effect during the first 142 days of the study (data not shown) as evidenced by a mean relative depot volume of 100% or more measured at this time point and all previous time points (day 28, day 61, day 84, day 114). After 168 days study duration a mean relative depot volume of compositions ID14 and ID15 of less than 100% was measured. After a certain time, a reduction of the depot volume is to be expected since the compositions are biodegradable. A comparison of the mean relative depot volume at day 84 and at day 168 is shown in Table 4.

TABLE 4

Mean relative depot volume measured on day 84 and day 168 in percent.

| ID | Mean relative depot volume [%] at day 84 | | Mean relative depot volume [%] at day 168 | |
|---|---|---|---|---|
|  | mean | S.D. | mean | S.D. |
| 12 | 130.15 | 48.48 | 111.29 | 46.47 |
| 13 | 140.74 | 42.90 | 126.01 | 54.22 |
| 14 | 121.51 | 21.89 | 95.64 | 23.67 |
| 15 | 112.14 | 24.48 | 95.81 | 26.23 |

The abbreviation S.D. stands for standard deviation.

Example 9—Formulation and Characterization of a Hydrogel Composition ID16 Comprising a Crosslinked Thiol-Modified Hyaluronan with a DoM of 176 µmol Thiol Groups Per g Polymer A thiol-modified hyaluronan with a degree of modification of 176 µmol thiol groups per g polymer (MMW 750 kDa) was used to produce a sterile hydrogel composition comprising 17.9 mg/mL crosslinked HA-cysteamine sodium salt, 3 mg/mL lidocaine HCl and 5 mg/mL unmodified sodium hyaluronate. The hydrogel composition ID16 was produced according to method A with a sieving step. Mean reduced post-sterilisation molecular weight (MRPMW) of crosslinked polymer in the composition was 408 kDa. The elastic modulus was determined in analogy to Example 6. The hydrogel was applied to the rheometer directly from the syringe (without needle attachment) and G' was determined to be 2,052,100 mPa. The sterile hydrogel had a pH of 7.17 and an osmolality of 316 mOsmol/kg.

The composition was tested in vivo similarily to the test set-up described above in Example 7 with 12 intradermal applications. The composition had a volumizing effect during 81 days study duration (data not shown) as evidenced by a mean relative depot volume of 100% or more measured at this time point and all previous time points (day 23, day 53).

Example 10—Formulation and Characterization of a Hydrogel Composition ID17 Comprising a Thiol-Modified Hyaluronan with a MRPMW of 300 kDa A thiol-modified hyaluronan with a degree of modification of 142 µmol thiol groups per g polymer (MMW 710 kDa) was used to produce a sterile hydrogel composition comprising 17.9 mg/mL crosslinked HA-cysteamine sodium salt, 3 mg/mL lidocaine HCl and 5 mg/mL unmodified sodium hyaluronate. The hydrogel composition ID17 was produced according to method A with a sieving step. Mean reduced post-sterilisation molecular weight (MRPMW) of crosslinked polymer in the composition was 300 kDa. The elastic modulus was determined in analogy to Example 4. The hydrogel was applied to the rheometer directly from the syringe (without needle attachment) and G' was determined to be 1,243,500 mPa. The sterile hydrogel had a pH of 7.65 and an osmolality of 287 mOsmol/kg. The composition was tested in vivo similarily to the test set-up described above in Example 7 with 12 intradermal applications. The composition had a volumizing effect during 133 days study duration (data not shown) as evidenced by a mean relative depot volume of 100% or more measured at this time point and all previous time points (day 23, day 53, day 81, day 107).

Example 11—Formulation and Characterisation of a Sterile Hydrogel Composition ID18

A sterile hydrogel composition (ID 18) comprising 14 mg/mL crosslinked HA-cysteamine, 3 mg/mL lidocaine HCl and 7 mg/mL unmodified sodium hyaluronate was produced according to method B. In brief, 2100 mg HA-cysteamine (dry weight, MMW 700 kDa, degree of modification 131 µmol/g polymer), 450 mg lidocaine HCl (dry weight) and 1050 mg sodium hyaluronate (dry weight, MMW 2238 kDa) were dissolved in 130 g 10 mM phosphate buffer pH 7.1 (comprising 88 mM NaCl) under mechanical stirring at room temperature for about 17 hours. After adjustment of the pH to about pH 7.1 with 1 M sodium hydroxide solution, 10 mM phosphate buffer pH 7.1 (comprising 88 mM NaCl) was added to a final amount of 150 g composition. The solution was homogenized for about 60 min. Then, 1.6 ml of a 0.307% (v/v) hydrogen peroxide solution were added. After incubation overnight at room temperature the crosslinked hydrogel was filled into 1 mL glass syringes and sterilized via autoclavation. The sterile hydrogel had a pH of about 7 and an osmolality of about 270 mOsmol/kg.

Degree of modification (DoM), MMW, MRPMW, and elastic modulus G' were determined as described above and are summarized in Table 5. For the determination of elastic modulus G' the hydrogel was applied to the rheometer directly from the syringe (without needle attachment)

TABLE 5

Characteristics of a hydrogel composition

| ID | MMW HA-SH raw material [kDa] Mean | MRPMW oxidized HA-SH [kDa] Mean | DoM HA-SH raw material [µmol/g] Mean | Elastic modulus G' [mPa] Mean |
|---|---|---|---|---|
| 18 | 700 | 618 | 131 | 1,162,567 |

Example 12—Synthesis of Thiol Group Bearing Modification Agents

A. Preparation of bis(Glycyl)-cystamine dihydrochloride:

To a mixture of cystamine dihydrochloride (1 g, 4.44 mmol) and N-(tert-Butoxycarbonyl)glycine (1.59 g, 9.10 mmol) in dry dichloromethane:THF=1:1 (20 mL) first triethylamine (1270 µL, 9.16 mmol) was added, followed by addition of a solution of EDC*HCl (1.75 g, 9.10 mmol) in dichloromethane. The reaction solution was stirred for 5 h at ambient temperature, then volatiles were evaporated under reduced pressure. The residue was taken up in ethyl acetate (250 mL) and washed with 1 N HCl (2×50 mL), half saturated NaHCO$_3$ (50 mL) and water (50 mL). The organic layer was dried over Na$_2$SO$_4$, volatiles were evaporated under reduced pressure to give the N-Boc protected bis(Glycyl)-cystamine as a colorless oil. Yield: 1.575 g (88%).

¹H NMR (400 MHZ, CDCl₃) δ 6.97 (s, 1H, NH), 5.53 (s, 1H, NH), 3.81 (d, J=5.8 Hz, 2H, α-C$\underline{H_2}$), 3.58 (aq, J=6.3 Hz, 2H, —C$\underline{H_2}$—NH—), 2.82 (t, 2H, —C$\underline{H_2}$—S—), 1.45 (s, 9H, —C$\underline{H_3}$ t-Bu); m/z=467.1 [M+H]⁺, 489.1 [M+Na]⁺.

To a solution of the N-Boc protected bis(Glycyl)-cystamine (300 mg, 0.64 mmol) in MeOH (5 mL) was added acetyl chloride (300 μL, 4.20 mmol). After the exothermic reaction had ceased, the mixture was stirred in a sealed flask for 5 h at ambient temperature, then toluene (2 mL) was added and volatiles were evaporated until the product precipitated. The white solid was isolated via suction filtration and washed with n-pentane (2×5 mL). Yield: 146 mg (67%). m.p.=184° ° C. (decomp.); ¹H NMR (400 MHZ, D20) δ 3.81 (s, 2H, α-C$\underline{H_2}$), 3.59 (at, J=6.3 Hz, 2H, —C$\underline{H_2}$—NH), 2.88 (at, 2H, —C$\underline{H_2}$—S—); m/z=266.9 [M+H]⁺, 288.9 [M+Na]⁺.

This modification agent allows the preparation of a hyaluronan-glycyl-cysteamine conjugate (FIG. 3 B).

B. Preparation of Dithiodiethanediyldicarbonyldiamino Diacetic Acid Dihydrazide (DGDTPDH):

To a mixture of 3,3'-dithiodipropionic acid (2 g, 9.5 mmol) and Glycine ethyl ester hydrochloride (2.66 g, 19.0 mmol) in dry dichloromethane:THF=1:1 (20 mL) was added triethylamine (2.78 μL, 20.0 mmol), followed by addition of a solution of EDC*HCl (3.83 g, 20.0 mmol) in dichloromethane. The reaction was stirred for 5 h at ambient temperature, then diluted with ethyl acetate (400 mL). The organic layer was washed with 1 N HCl (2×50 mL), half saturated NaHCO₃ (50 mL) and water (50 mL), then dried over Na₂SO₄ and volatiles were evaporated under reduced pressure to give dithiodiethanediyldicarbonyldiamino diacetic acid diethylester as a white solid. Yield: 1.69 g (47%); m.p.=121° C.; ¹H NMR (400 MHZ, CDCl₃) δ 6.50 (s, 1H, NH), 4.21 (q, J=7.1 Hz, 2H, —O—C$\underline{H_2}$—), 4.04 (d, J=5.3 Hz, 2H, α-C$\underline{H_2}$—N), 2.99 (t, J=7.0 Hz, 2H, —C$\underline{H_2}$—S—), 2.67 (t, 2H, α-C$\underline{H_2}$—CH₂—), 1.28 (t, 3H, —C$\underline{H_3}$); m/z=381.0 [M+H]⁺, 403.0 [M+Na]⁺.

A mixture of the diethylester (500 mg, 1.32 mmol) and 80% aq. hydrazine hydrate (0.5 mL, 12.7 mmol) in 96% EtOH was refluxed for 5 h. The product crystallized upon cooling to ambient temperature and was collected via suction filtration and washed thoroughly with cold EtOH (2×15 mL). Yield: 335 mg (72%), white needles. m.p.=197° C. (decomp.) ¹H NMR (400 MHZ, DMSO-d6) δ 9.02 (s, 1H, —NH), 8.20 (t, J=5.7 Hz, 1H, —NH), 4.19 (s, 2H, —NH₂), 3.64 (d, J=5.8 Hz, 2H, α-C$\underline{H_2}$—N), 2.87 (t, J=7.2 Hz, 2H, —C$\underline{H_2}$—S—), 2.53 (t, 2H, α-C$\underline{H_2}$—CH₂—); m/z=353.1 [M+H]⁺, 375.1 [M+Na]⁺.

This modification agent allows the preparation a hyaluronan-2-mercapto-ethyl-carbonyl-amino-acetic acid hydrazide conjugate (FIG. 3 D).

C. Preparation of 4,4'-Dithiobis[1-butanamine]dihydrochlorid 4,4'-Dithiobis[1-butanamine] dihydrochlorid was prepared from 4-aminobutan-1-ol following protocols reported in literature (Aufort, M. et. al., ChemBioChem, 12(4), 583-592, 2011), final N-Boc deprotection was adopted and carried out with MeOH/HCl to obtain the product as dihydrochlorid salt instead: To a solution of dicarbamate (550 mg, 1.35 mmol) in methanol (6 mL) was added acetylchloride (0.6 mL, 8.4 mmol) dropwise. When the exothermic reaction had ceased, the mixture was refluxed for 5 h. Then toluene was added (6 mL) and the mixture was concentrated under reduced pressure. The crude product was repeatedly azeotroped with toluene (6 mL), then isolated via suction filtration and washed with n-pentane (2×6 mL) Yield: 340 mg (90%), white solid. m.p.=249° C. (decomp.); ¹H NMR (400 MHz, D2O+DSS) δ 3.02 (t, J=7.1 Hz, 4H, C$\underline{H_2}$—N), 2.78 (t, J=6.7 Hz, 4H, —C$\underline{H_2}$—S—), 1.83-1.71 (m, 8H, C—C$\underline{H_2}$—C$\underline{H_2}$—C); m/z=209.0 [M+H].

This modification agent allows the preparation of a N-mercapto-n-butylhyaluronamide (FIG. 3 C).

Example 13—Formulation and Characterisation of a Hydrogel Composition Comprising Crosslinked hyaluronan-glycyl-cysteamine A hydrogel composition (ID 19) comprising 17.9 mg/mL crosslinked hyaluronan-glycyl-cysteamine sodium salt (HA-GLYC) and 5 mg/mL unmodified sodium hyaluronate was produced according to method B without addition of lidocaine HCl. In brief, 537 mg HA-GLYC (dry weight, MMW 610 kDa, degree of modification 162 μmol/g polymer, FIG. 3 B) and 150 mg sodium hyaluronate (dry weight, MMW 2.4 MDa) were dissolved in 26 g 0.01 M HCl (comprising NaCl) under mechanical stirring at room temperature for about 5 hours. To 19.02 g of this solution, were added 2.115 mL of 100 mM phosphate buffer pH 11.85, which resulted in an adjustment of the pH to about pH 7.4. Then 273 μL of a 0.3% H₂O₂ solution was added and the mixture was homogenized for 15 min at ambient temperature and then left overnight for crosslinking. The crosslinked hydrogel was filled into 1 mL glass syringes and sterilized via autoclavation. The sterile hydrogel had a pH of about 7.2.

Degree of modification (DoM), MMW, residual thiol content, and elastic modulus G' were determined as described above and are summarized in Table 6. For the determination of elastic modulus G' the hydrogel was applied to the rheometer directly from the syringe (without needle attachment).

TABLE 6

Characteristics of a hydrogel composition

| ID | MMW HA-SH raw material [kDa] Mean | DoM HA-SH raw material [μmol/g] Mean | Residual thiol content [μmol/g] Mean | Elastic modulus G' [mPa] Mean |
|---|---|---|---|---|
| 19 | 610 | 162 | 0 | 1,260,467 |

Example 14—Formulation and Characterisation of a Sterile Hydrogel Composition Comprising Crosslinked hyaluronan-homocysteine A hydrogel composition (ID 20) comprising 17.9 mg/mL crosslinked hyaluronan-homocysteine sodium salt (HA-HCYS) and 5 mg/mL unmodified sodium hyaluronate was produced according to method A without addition of lidocaine HCl. In brief, 537 mg HA-HCYS (FIG. 3A, dry weight, MMW 610 kDa, degree of modification 136 μmol/g polymer, FIG. 3A) and 150 mg sodium hyaluronate (dry weight, MMW 2.4 MDa) were dissolved in 26 g 0.01 M HCl (comprising NaCl) under mechanical stirring at room temperature for about 5 hours followed by 1 hour resting time to remove air bubbles. To 23.68 g of the solution, 2.63 ml 100 mM phosphate buffer pH 12.04 was added, which resulted in an adjustment of the pH of the solution to about pH 7.2. The mixture was left for 48 h at room temperature for crosslinking, then the crosslinked hydrogel was filled into 1 mL glass syringes and sterilized via auto lavation. The sterile hydrogel had a pH of about 7.0.

Degree of modification (DoM), MMW, residual thiol content, and elastic modulus G' were determined as described above and are summarized in Table 7. For the determination of elastic modulus G' the hydrogel was applied to the rheometer directly from the syringe (without needle attachment).

TABLE 7

| | Characteristics of a hydrogel composition | | | |
|---|---|---|---|---|
| ID | MMW HA-SH raw material [kDa] Mean | DoM HA-SH raw material [µmol/g] Mean | residual thiol content [µmol/g] Mean | Elastic modulus G' [mPa] Mean |
| 20 | 610 | 136 | 0 | 1,759,900 |

Example 15—Formulation and Characterisation of a Sterile Hydrogel Composition Comprising Crosslinked hyaluronan-2-mercapto-ethyl-carbonyl-amino-acetic acid hydrazide A sterile hydrogel composition (ID 21) comprising 17.9 mg/mL crosslinked hyaluronan-2-mercapto-ethyl-carbonyl-amino-acetic acid hydrazide sodium salt (HA-DGDTPDH) and 5 mg/mL unmodified sodium hyaluronate was produced according to method B without addition of lidocaine HCl. In brief, 537 mg HA-DGDTPDH (FIG. 3 D, dry weight, MMW 770 kDa, degree of modification 134 µmol/g polymer) and 150 mg sodium hyaluronate (dry weight, MMW 2.4 MDa) were dissolved in 26 g 0.01 M HCl (comprising 192 mg NaCl) under mechanical stirring at room temperature for about 5 h. To 20.20 g of this solution, 2.25 ml 100 mM phosphate buffer pH 12.07, containing 0.041% $H_2O_2$ was added, which resulted in an adjustment of the pH of the solution to about pH 7.0. The mixture was left for 18 h at room temperature for crosslinking. The crosslinked hydrogel was then filled into 1 mL glass syringes and sterilized via autoclavation. The sterile hydrogel had a pH of about 7.0 and an osmolality of 326 mOsmol/kg.

Degree of modification (DoM), MMW, residual thiol content, and elastic modulus G' were determined as described above and are summarized in Table 8. For the determination of elastic modulus G' the hydrogel was applied to the rheometer directly from the syringe (without needle attachment).

TABLE 8

| | Characteristics of a hydrogel composition | | | |
|---|---|---|---|---|
| ID | MMW HA-SH raw material [kDa] Mean | DoM HA-SH raw material [µmol/g] Mean | residual thiol content [µmol/g] Mean | Elastic modulus G' [mPa] Mean |
| 21 | 770 | 134 | 0 | 698,860 |

Example 16—Formulation and Characterisation of a Hydrogel Composition Comprising Crosslinked N-mercapto-n-butylhyaluronamide A sterile hydrogel composition (ID 22) comprising 17.9 mg/mL crosslinked N-mercapto-n-butylhyaluronamide sodium salt and 5 mg/mL unmodified sodium hyaluronate was produced according to method B without addition of lidocaine HCl. In brief, 537 mg N-mercapto-n-butylhyaluronamide sodium salt (FIG. 3 C, dry weight, MMW 767 kDa, degree of modification 98 µmol/g polymer) and 150 mg sodium hyaluronate (dry weight, MMW 2.4 MDa) were dissolved in 26 g 0.01 M HCl (comprising NaCl) under mechanical stirring at room temperature for about 5 hours. To 23.48 g of this solution, were added 2.609 mL of 100 mM phosphate buffer pH 11.81, containing 0,029% $H_2O_2$, which resulted in an adjustment of the pH to about pH 7.1. The mixture was homogenized for 15 min at room temperature and then left overnight to complete crosslinking. The crosslinked hydrogel was filled into 1 mL glass syringes and sterilized via autoclavation. The sterile hydrogel had a pH of about 7.0 and an osmolality of 351 mOsmol/kg.

Degree of modification (DoM), MMW, residual thiol content, and elastic modulus G' were determined as described above and the mean values are summarized in Table 9. For the determination of elastic modulus G' the hydrogel was applied to the rheometer directly from the syringe (without needle attachment).

TABLE 9

| | Characteristics of a hydrogel composition | | | |
|---|---|---|---|---|
| ID | MMW HA-SH raw material [kDa] Mean | DoM HA-SH raw material [µmol/g] Mean | residual thiol content [µmol/g] Mean | Elastic modulus G' [mPa] Mean |
| 22 | 767 | 98 | 1 | 839,510 |

Example 17—Optimizing Conditions for Crosslinking of Thiol-Modified Hyaluronan at an Industrial Scale A thiol-modified hyaluronan with a degree of modification of 140 µmol thiol groups per g polymer (MMW 820 kDa) was used to produce a hydrogel composition comprising 17.9 mg/mL crosslinked HA-cysteamine sodium salt, 3 mg/mL lidocaine HCl and 5 mg/mL unmodified sodium hyaluronate at an industrial scale (batch size 17.5 kg). After dissolving HA-cysteamine sodium salt, lidocaine HCl, unmodified sodium hyaluronate and sodium chloride in 0.01 M HCl via stirring for about 8 h at room temperature, the solution was divided in two parts.

One part (7560 g) of the solution was incubated overnight under vacuum in vessel B. Crosslinking was initiated by addition of one part of a 100 mM phosphate buffer pH 12.3 to 9 parts solution, followed by addition of a solution comprising hydrogen peroxide, so that the molar ratio of free thiol groups of thiol-modified hyaluronan to hydrogen peroxide was 2:1 (compare method B). The resulting pH of the solution in vessel B was 7.7 and the osmolality was 316 mOsmol/kg.

The second part (5800 g) of the solution was also incubated overnight under vacuum in vessel A, followed by crosslinking by addition of one part of a 100 mM phosphate buffer pH 12.3 to 9 parts solution (compare method A; vessel A). Instead of a solution comprising hydrogen peroxide water for injection was added to the bulk in a corresponding amount. The resulting pH of the solution in vessel A was 7.7 and the osmolality was 312 mOsmol/kg.

After brief homogenization via stirring for 10 minutes both vessels were kept at room temperature. To provide oxygen for crosslinking, an excess air pressure of +1 bar was applied to vessel A during the entire crosslinking period of 10 days (a brief interruption in the period of 72h to 96h after initiation of crosslinking was due to technical problems).

Samples were drawn at the time points and locations listed in the table below. The surface sample was taken from the hydrogel in the vessel close to the surface, whereas the bottom sample was taken from the lower part of the hydrogel near to the bottom of the vessel. The elastic modulus was measured as described in example 4 (samples were not filled in syringes).

TABLE 10

Comparison of elastic properties of hydrogels produced under different crosslinking conditions

| | method A/vessel A | | method B/vessel B | |
| --- | --- | --- | --- | --- |
| Days of crosslinking | Surface sample G' [mPa] | Bottom sample G' [mPa] | Surface sample G' [mPa] | Bottom sample G' [mPa] |
| 3 | 531,255 | 313,810 | 2,670,550 | 2,657,800 |
| 4 | 1,500,200 | 425,365 | n.d. | n.d. |
| 5 | 1,685,750 | 491,345 | n.d. | n.d. |
| 6 | n.d. | n.d. | 2,548,750 | 2,546,000 |
| 10 | 2,269,100 | 762,660 | n.d. | n.d. |

The elastic modulus was used as a parameter to monitor the firmness of the hydrogels, which is known to be increased by crosslinking. The first sample was obtained directly after initiation of crosslinking. The clastic modulus G' of the sample obtained from vessel A was 33,729 mPa. In contrast, the clastic modulus of the sample obtained from vessel B 2,475,700 mPa, indicating that crosslinking had proceeded much faster in the presence of the oxidation agent hydrogen peroxide. The data listed in table 10 further demonstrate that the crosslinking reaction did not proceed homogenously throughout the entire bulk during an incubation time of 10 days when production method A was used at an industrial scale. The application of excess air pressure to the vessel resulted in more efficient crosslinking only at the surface of the bulk in vessel A. In contrast, the provision of oxygen in a sufficient amount via addition of hydrogen peroxide resulted in an almost instantaneous and homogenous crosslinking reaction (method B; vessel B).

Example 18—Monitoring Formation of Disulfide Bonds During Crosslinking Via Determination of Residual Thiol Group Content A thiol-modified hyaluronan with a degree of modification of 140 µmol thiol groups per g polymer (MMW 820 kDa) was used to produce a hydrogel composition comprising 17.9 mg/mL crosslinked HA-cysteamine sodium salt, 3 mg/mL lidocaine HCl and 5 mg/mL unmodified sodium hyaluronate. After dissolving HA-cysteamine sodium salt, lidocaine HCl, unmodified sodium hyaluronate and sodium chloride in 0.01 M HCl via stirring for about 16 h at room temperature, the solution was divided in four equal parts weighing about 160 g each. To each solution about 20 g of 100 mM phosphate buffer pH 12 was added under stirring. After 15 minutes homogenization 20 g of diluted hydrogen peroxide solution was added to each of the four solutions, so that for producing hydrogel E100 the molar ratio of free thiol groups of thiol-modified hyaluronan to hydrogen peroxide was 2:1; during production of hydrogel E50 (comprising 50% of the hydrogen peroxide concentration of E100) the molar ratio of free thiol groups of thiol-modified hyaluronan to hydrogen peroxide was 4:1; during production of hydrogel E30 (comprising 30% of the hydrogen peroxide concentration of E100) the molar ratio of free thiol groups of thiol-modified hyaluronan to hydrogen peroxide was about 7:1; during production of hydrogel E10 (comprising 10% of the hydrogen peroxide concentration of E100) the molar ratio of free thiol groups of thiol-modified hyaluronan to hydrogen peroxide was 20:1. After a brief homogenisation the crosslinking reaction was 5 performed at room temperature without further stirring.

Samples were drawn at the time points listed in the table below. The residual thiol group content and the elastic modulus were measured as described above (samples were not filled in syringes). The residual thiol content in % was calculated from the initial degree of modification of the thiol-modified hyaluronan (140 µmol thiol groups per g polymer).

TABLE 11

Monitoring of crosslinking efficiency via measurement of residual thiol group content and elastic modulus G' of samples

| Hydrogel E100 | | | |
| --- | --- | --- | --- |
| Days of crosslinking | G' [mPa] | Residual thiol content [µmol/g] | Residual thiol content [%] |
| 0 | 1,703,300 | n.d. | n.d. |
| 1 | 2,928,500 | 0 | 0 |
| 2 | 3,055,900 | 0 | 0 |
| 3 | n.d. | n.d. | n.d. |
| 7 | n.d. | n.d. | n.d. |

| Hydrogel E50 | | | |
| --- | --- | --- | --- |
| Days of crosslinking | G' [mPa] | Residual thiol content [µmol/g] | Residual thiol content [%] |
| 0 | 947,745 | n.d. | n.d. |
| 1 | 2,191,950 | 43.9 | 31 |
| 2 | 2,217,000 | 31.8 | 23 |
| 3 | 2,415,800 | 17.7 | 13 |
| 7 | 2,642,350 | n.d. | n.d. |

| Hydrogel E30 | | | |
| --- | --- | --- | --- |
| Days of crosslinking | G' [mPa] | Residual thiol content [µmol/g] | Residual thiol content [%] |
| 0 | 707,515 | n.d. | n.d. |
| 1 | 1,514,500 | 115.5 | 83 |
| 2 | 1,795,300 | 53.2 | 38 |
| 3 | 1,975,100 | 32.4 | 23 |
| 7 | 2,415,700 | n.d. | n.d. |

| Hydrogel E10 | | | |
| --- | --- | --- | --- |
| Days of crosslinking | G' [mPa] | Residual thiol content [µmol/g] | Residual thiol content [%] |
| 0 | 321,695 | n.d. | n.d. |
| 1 | 512,500 | 122.7 | 88 |
| 2 | 827,810 | 88.7 | 63 |
| 3 | 1,326,400 | 47.2 | 33 |
| 7 | 2,023,800 | n.d. | n.d. |

The elastic modulus G' of the samples was observed to reach a plateau (G' in the range of from 2400 Pa to 3000 Pa) when the residual thiol content in the hydrogel was less than 20%. Crosslinking of hydrogel E100 was completed within 2 days. When using a 50% lower concentration of hydrogen peroxide for crosslinking (hydrogel E50) the crosslinking reaction took about 3 days. Using a 90% lower concentration of hydrogen peroxide for crosslinking (hydrogel E10) crosslinking was not completed even after 7 days.

The invention claimed is:

1. A sterile hydrogel composition comprising:
a crosslinked polymer,
wherein the crosslinked polymer is an oxidation product of a thiol-modified hyaluronan,
wherein the thiol-modified hyaluronan has a degree of modification with thiol groups of more than about 80 μmol per gram of polymer,
wherein the thiol-modified hyaluronan has a degree of modification with thiol groups of less than about 280 μmol per gram of polymer, and
wherein the composition has a residual thiol content of less than 20% with respect to the degree of modification of the thiol-modified hyaluronan, and
wherein the thiol-modified hyaluronan has a molecular weight of at least about 400 kDa and the thiol-modified hyaluronan is included in the composition with a concentration of from about 11 mg/mL to about 20 mg/mL.

2. The composition according to claim 1, wherein the composition has a residual thiol content of less than 15% in respect to the degree of modification of the thiol-modified hyaluronan.

3. The composition according to claim 1, wherein the thiol-modified hyaluronan is included in the composition with a concentration of from about 13 mg/mL to about 18 mg/mL.

4. The composition according to claim 1, wherein the thiol-modified hyaluronan has a molecular weight of at least about 500 kDa.

5. The composition according to claim 1, wherein the crosslinked polymer has a mean reduced post-sterilisation molecular weight of more than about 250 kDa, wherein the mean reduced post-sterilisation molecular weight is defined as the mean molecular weight of a reduced thiol-modified hyaluronan from said sterile hydrogel composition after exposing said crosslinked polymer to reductive conditions.

6. The composition according to claim 1, wherein the thiol-modified hyaluronan is a conjugate of a modification agent linked to hyaluronan via an amide bond, wherein the agent is selected from the group comprising glutathione, aminoalkylthiols comprising a $C_2$-$C_6$-linear or branched alkyl chain, cysteine, homocysteine, amino acid derivatives of cysteamine, cysteine and homocysteine, carboxylate esters of homocysteine and carboxylate esters of cysteine.

7. The composition according to claim 1, wherein the thiol-modified hyaluronan is a hyaluronan-cysteamine conjugate (HA-cysteamine).

8. The composition according to claim 1, wherein the composition further comprises an unmodified polymer selected from the group of biocompatible polysaccharides.

9. The composition according to claim 1, wherein the composition has an elastic modulus G' of at least about 900 Pa, measured at 25° C. using a shear rate of 1 Hz.

10. A medicine comprising the composition according to claim 1 for use as medicine.

11. A soft tissue filler comprising the composition according to claim 1.

12. A method of tissue augmentation comprising applying the composition according to claim 1 to augment soft tissue of a recipient in need thereof.

13. A method for treatment or prevention of disease comprising administering the composition according to claim 1 to a recipient in need thereof in the treatment or prevention of a disease selected from the group consisting of metatarsalgia, urinary or faecal incontinence, vulvovaginal atrophy, vocal cord impairment, venous valve insufficiency, facial lipoatrophy, debilitating scars, and morphological asymmetry or deformation.

14. A method of cosmetic alteration comprising applying the composition according to claim 1 to a recipient in need thereof.

15. The method according to claim 14, wherein the composition is applied to the recipient as a soft tissue filler.

16. The method according to claim 14, comprising at least one of filling wrinkles, filling skin defects, restoring lost volume of the face or the body, reducing dimples in cellulitis, or shaping contours of the face or the body.

17. A method for producing a sterile hydrogel composition, comprising the steps of:
a) providing a thiol-modified hyaluronan in an aqueous solution,
wherein the thiol-modified hyaluronan has a degree of modification with thiol groups of more than about 80 μmol per gram of polymer, and
wherein the thiol-modified hyaluronan has a degree of modification with thiol groups of less than about 280 μmol per gram of polymer, and
wherein the thiol-modified hyaluronan has a molecular weight of at least about 400 kDa,
b) oxidizing the thiol-modified hyaluronan by exposing the previously obtained aqueous solution to conditions that allow the thiol-modified hyaluronan to form a crosslinked polymer, wherein the aqueous solution becomes a hydrogel, which hydrogel has a residual thiol content of less than 20% with respect to the degree of modification of the thiol-modified hyaluronan,
optionally c) adding an unmodified polymer selected from the group of biocompatible polysaccharides to the previously obtained hydrogel or to the previously obtained solution,
optionally d) sieving the previously obtained hydrogel to obtain a hydrogel with a particular particle sizes,
e) filling the previously obtained hydrogel into a container and exposing the filled container to conditions allowing for sterilization of the hydrogel, and
f) obtaining a sterile hydrogel composition in a container comprising the crosslinked polymer of the thiol-modified hyaluronan with a concentration of from about 11 mg/mL to about 20 mg/mL.

18. The method for producing a hydrogel composition according to claim 17, wherein the steps are conducted according to a sequence selected from the group consisting of:
a), b), c), d), e) and f)
a), b), d), c), e), and f)
a), b), c), e) and f)
a), b), d), e), and f)
a), c), b), d), e) and f) and
a), c), b), e) and f).

19. The method for producing a hydrogel composition according to claim 17, wherein in step b) an oxidation agent is added to the previously obtained aqueous solution.

20. The method for producing a hydrogel composition according to claim 17, further comprising a step of adding an anaesthetic agent and/or one or more additional components to the solution during step a) or to the hydrogel obtained in optional step c), or optional step d) or adding an anaesthetic agent and/or one or more additional components during step a) or during optional step c).

* * * * *